United States Patent
Slaby et al.

(10) Patent No.: US 10,758,669 B2
(45) Date of Patent: Sep. 1, 2020

(54) ANTI-OCCLUSION INTRAVENOUS TUBE PORT

(71) Applicants: Baxter International Inc., Deerfield, IL (US); Baxter Healthcare SA, Glattpark (Opfikon) (CH)

(72) Inventors: Jiri Slaby, Buffalo Grove, IL (US); James Thomas Maerzke, Kenosha, WI (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 136 days.

(21) Appl. No.: 15/855,550

(22) Filed: Dec. 27, 2017

(65) Prior Publication Data
US 2018/0185569 A1    Jul. 5, 2018

Related U.S. Application Data

(60) Provisional application No. 62/440,738, filed on Dec. 30, 2016.

(51) Int. Cl.
*A61M 5/142* (2006.01)
*A61M 5/168* (2006.01)
*A61M 39/28* (2006.01)

(52) U.S. Cl.
CPC ........ *A61M 5/142* (2013.01); *A61M 5/14228* (2013.01); *A61M 5/16831* (2013.01); *A61M 39/288* (2013.01); *A61M 2206/20* (2013.01)

(58) Field of Classification Search
CPC .... A61M 2205/0216; A61M 2205/121; A61M 5/14228; A61M 5/14212; A61M 5/142;
(Continued)

(56) References Cited

U.S. PATENT DOCUMENTS

| 4,257,422 A | 3/1981 | Duncan |
| 4,689,043 A | 8/1987 | Bisha |

(Continued)

FOREIGN PATENT DOCUMENTS

| EP | 0293241 | 11/1988 |
| EP | 2712653 | 4/2014 |
| JP | H1037820 | 2/1998 |

OTHER PUBLICATIONS

International Search Report—PCT/US2017/068554 dated Mar. 28, 2018—7 pages.

(Continued)

*Primary Examiner* — Jason E Flick

(74) *Attorney, Agent, or Firm* — K&L Gates LLP

(57) ABSTRACT

An infusion pump includes a housing. The housing includes a tube port adapted to receive an intravenous ("IV") tube. The tube port includes a tube channel and a rib. The tube channel has an inlet and an outlet end. The rib is positioned along the channel adjacent the outlet end. The rib is formed to extend towards the tube when the tube is passed through the tube port thereby indenting the tube and tending to prevent full occlusion of the tube. The tube port may also include a plurality of ribs positioned around a perimeter of the tube port on the exterior side of the housing. The plurality of ribs are configured to prevent an occlusion in the tube when the tube is bent on the exterior side of the housing.

20 Claims, 23 Drawing Sheets

(58) Field of Classification Search
CPC ......... A61M 5/168; F04B 43/12; F04B 53/16; F04B 43/00; F04B 43/08; F04B 53/00; F16J 15/104; F16J 15/00; F16J 15/002; F16J 15/05
USPC ........................................................ 604/151
See application file for complete search history.

(56) References Cited

U.S. PATENT DOCUMENTS

| | | |
|---|---|---|
| 5,215,450 A | 6/1993 | Tamari |
| 5,336,190 A | 8/1994 | Moss et al. |
| 5,823,746 A | 10/1998 | Johnson |
| 5,868,712 A | 2/1999 | Briggs et al. |
| 6,007,941 A | 12/1999 | Hermann et al. |
| 6,261,262 B1 * | 7/2001 | Briggs .................. A61M 5/142 251/7 |
| 6,629,955 B2 | 10/2003 | Morris et al. |
| 6,907,830 B2 | 6/2005 | Guinan et al. |
| 6,942,473 B2 | 9/2005 | Abrahamson et al. |
| 7,611,498 B2 | 11/2009 | Hasler |
| 7,935,081 B2 | 5/2011 | Flaker et al. |
| 8,096,628 B2 | 1/2012 | Ostrowski |
| 8,118,778 B2 | 2/2012 | Haylor et al. |
| 8,257,066 B2 | 9/2012 | Kasai et al. |
| 8,308,457 B2 | 11/2012 | Rotem et al. |
| 8,430,654 B2 | 4/2013 | Kasai et al. |
| 2009/0306592 A1 | 12/2009 | Kasai et al. |
| 2011/0318208 A1 | 12/2011 | Goldor et al. |
| 2012/0078185 A1 | 3/2012 | Smith et al. |
| 2012/0101438 A1 | 4/2012 | Gagliardoni et al. |
| 2012/0238991 A1 | 9/2012 | Zhang et al. |
| 2014/0271247 A1 | 9/2014 | Abal |
| 2014/0276424 A1 | 9/2014 | Davis et al. |

OTHER PUBLICATIONS

Written Opinion of the International Searching Authority—PCT/US2017/068554 dated Mar. 28, 2018—7 pages.

* cited by examiner

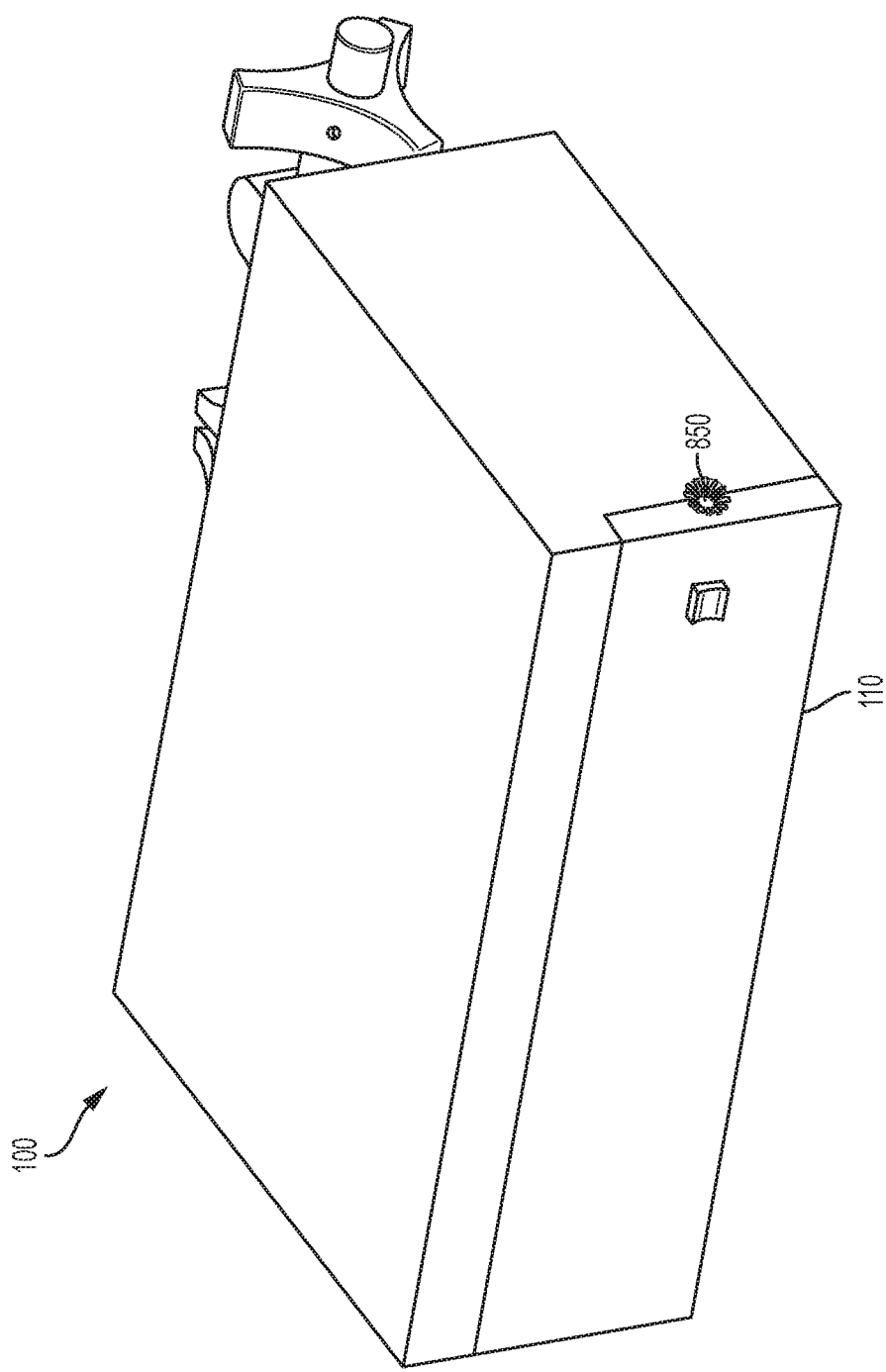

US 10,758,669 B2

ANTI-OCCLUSION INTRAVENOUS TUBE PORT

PRIORITY CLAIM

This application claims priority to and the benefit as a non-provisional application of U.S. Provisional Patent Application No. 62/440,738, entitled "Anti-Occlusion Intravenous Tube Port", filed Dec. 30, 2016, the entire contents of which is hereby incorporated by reference and relied upon.

BACKGROUND

Infusion pumps deliver fluids (e.g., drugs or medication) to patients over an extended period of time. Specifically, infusion pumps may be used to administer drugs to patients over long durations, which may be prohibitive to administer by direct injection. Infusion pumps may deliver fluids (e.g., medications) through an intravenous ("IV") tube, which due to various reasons may become blocked or occluded.

Tube occlusions are problematic because they may cause an infusion pump to display an erroneous volume infused. Additionally, an inaccurate record of total volume infused may result in an inappropriate clinical decision when prescribing further IV therapy. Additionally, a tube occlusion may delay the administration of critical medications. Delaying the administration of medications to patients may cause complications and negatively affect the patient's health. For example, delaying the administration of fast-acting drugs (e.g., dopamine, oxytocin, nitroprusside), such as a pain reliever, may cause the patient to experience pain for a longer period of time until the occlusion is remedied. Additionally, the result of delaying the administration of slower-acting drugs, whose effects are not immediately recognized (e.g., heparin, insulin, lidocaine) and may not be realized for several hours, may further delay the effects of the drug. By the time the drug is properly administered, it may take another several hours before the patient receives the benefit of the drug.

SUMMARY

The present disclosure provides improved infusion pump housings with anti-occlusion intravenous ("IV") tube ports. The anti-occlusion IV tube ports prevent full elastomeric IV tube occlusion where the tube exits the pump, and is particularly useful in instances when the tube exits the pump at a sharp exit angle. The tube port may include one or more gradually increasing rib(s) to ensure that when the IV tube is bent leaving the pump, it is divided into two or more regions that do not fully collapse, thereby allowing the liquid (e.g., medication) to continue flowing through the tube to the patient. The gradual increase in the rib(s) profile ensures that the IV tube does not occlude fully, even if the tube is bent or twisted in multiple directions relative to the pump housing. The anti-occlusion IV tube port may include multiple ribs. For example, multiple ribs strategically spaced on the exterior of the pump housing may advantageously prevent IV tube collapse and occlusion when the tube is bent at varying exit angles.

Aspects of the subject matter described herein may be useful alone or in combination with any one or more of the other aspect described herein. Without limiting the foregoing description, in a first aspect of the present disclosure, which may be combined with any other aspect listed herein unless specified otherwise, an infusion pump includes a housing, which includes a tube port adapted to receive an IV tube. The tube port includes a tube channel and a rib. The channel has an inlet end and an outlet end. The rib is positioned along the channel adjacent the outlet end. Additionally, the rib is formed to extend towards the tube when the tube is passed through the tube port thereby indenting the tube and tending to prevent full occlusion of the tube.

In a second aspect of the present disclosure, which may be combined with any other aspect listed herein unless specified otherwise, the rib is configured to split the tube channel into a first channel and a second channel.

In a third aspect of the present disclosure, which may be combined with any other aspect listed herein unless specified otherwise, the tube channel is positioned along an interior wall of the housing and is at least substantially perpendicular to the tube port.

In a fourth aspect of the present disclosure, which may be combined with any other aspect listed herein unless specified otherwise, the tube channel is positioned along an interior wall of the housing and is at least substantially parallel to the tube port.

In a fifth aspect of the present disclosure, which may be combined with any other aspect listed herein unless specified otherwise, the infusion pump is configured such that the tube extends along the tube channel when the tube is pressed through the tube port.

In a sixth aspect of the present disclosure, which may be combined with any other aspect listed herein unless specified otherwise, a housing for an infusion pump includes a tube port adapted to receive an IV tube. The tube port includes a tube channel and a rib. The tube channel has an inlet end and an outlet end. The rib is positioned along the channel adjacent the outlet end. Additionally, the rib is formed to extend towards the tube as the tube is passed through the tube port, thereby indenting the tube and tending to prevent full occlusion of the tube.

In a seventh aspect of the present disclosure, which may be combined with any other aspect listed herein unless specified otherwise, the rib may be configured to split the tube channel into a first channel and as second channel.

In an eighth aspect of the present disclosure, which may be combined with any other aspect listed herein unless specified otherwise, the tube channel may be positioned along an interior wall of the housing and may be at least substantially perpendicular to the tube port.

In a ninth aspect of the present disclosure, which may be combined with any other aspect listed herein unless specified otherwise, the tube channel may be positioned along an interior wall of the housing and is at least substantially parallel to the tube port.

In a tenth aspect of the present disclosure, which may be combined with any other aspect listed herein unless specified otherwise, the rib may include a first end and a second end, the first end having a first diameter and the second end having a second, different diameter.

In an eleventh aspect of the present disclosure, which may be combined with the previous aspect in combination with any other aspect listed herein unless specified otherwise, the second diameter may be larger than the first diameter.

In a twelfth aspect of the present disclosure, which may be combined with any other aspect listed herein unless specified otherwise, the rib may include a gradually increasing profile from a first end to a second end, the first end closer to an outside opening of the port than the second end.

In a thirteenth aspect of the present disclosure, which may be combined with any other aspect listed herein unless specified otherwise, the rib may be formed to divide the IV tube into two un-occluded regions.

In a fourteenth aspect of the present disclosure, which may be combined with any other aspect listed herein unless specified otherwise, the rib may be positioned on the interior side of the housing.

In a fifteenth aspect of the present disclosure, which may be combined with any other aspect listed herein unless specified otherwise, the rib may be positioned on the exterior side of the housing.

In a sixteenth aspect of the present disclosure, which may be combined with any other aspect listed herein unless specified otherwise, an infusion pump includes a housing having includes a tube port extending through a wall of the housing. The tube port is configured to receive an intravenous ("IV") tube. The tube port includes a plurality of ribs positioned around a perimeter of the tube port on the exterior side of the housing. Additionally, the plurality of ribs may be configured to prevent an occlusion in the tube when the tube is bent on the exterior side of the housing.

In seventeenth aspect of the present disclosure, which may be combined with any other aspect listed herein unless specified otherwise, a plurality of ribs may be circumferentially positioned around the perimeter and are each pointed toward a center of the port.

In an eighteenth aspect of the present disclosure, which may be combined with any other aspect listed herein unless specified otherwise, each of a plurality of ribs may have at least approximately the same size and shape.

In a nineteenth aspect of the present disclosure, which may be combined with any other aspect listed herein unless specified otherwise, a plurality of ribs may include a first rib and a second rib, the first rib having a different size, shape and/or orientation than the second rib.

In a twentieth aspect of the present disclosure, which may be combined with any other aspect listed herein unless specified otherwise, a plurality of ribs each extend radially towards a center of the port.

In a twenty-first aspect of the present disclosure, which may be combined with any other aspect listed herein unless specified otherwise, an infusion pump includes a housing, which includes a tube port adapted to receive an intravenous ("IV") tube. The tube port includes a tube channel and a rib. The channel has an inlet end and an outlet end. The rib is positioned along the channel adjacent the outlet end. Additionally, the rib is formed to extend away from the channel.

In a twenty-second aspect of the present disclosure, any structure and functionality associated with any one or more, or all of FIGS. 1 to 19C may be combined with any structure and functionality associated with any other one or more, or all of FIGS. 1 to 19C.

To the extent that any of these aspects are mutually exclusive, it should be understood that such mutual exclusivity shall not limit in any way the combination of such aspects with any other aspects whether or not such aspect is explicitly recited. Any of these aspects may be claimed, without limitation, as a system, method, apparatus, device, medium, etc.

In light of the above aspects and description herein, it is accordingly an advantage of the present disclosure to prevent elastomeric intravenous tube occlusion when an IV tube exits an infusion pump.

It is another advantage of the present disclosure to divide the tube into two regions that do not fully collapse.

It is a further advantage of the present disclosure to prevent tube occlusion by ensuring that the tube does not abruptly collapse.

It is yet a further advantage of the present disclosure to prevent tube occlusion for several tube exit angles.

It is yet another advantage of the present disclosure to prevent tube occlusion for existing intravenous tube sets.

It is still a further advantage of the present disclosure to prevent tube occlusion without changing clinical treatment steps.

Additional features and advantages of the disclosed infusion pump and housing including an anti-occlusion tube port are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIG. 15 is an isometric view of an infusion pump according to an example embodiment of the present disclosure.

DETAILED DESCRIPTION OF EXAMPLE EMBODIMENTS

As discussed herein, improved infusion pump housings with anti-occlusion intravenous tube ports are provided to prevent intravenous tube occlusion upon the tube exiting the pump. Tube occlusions are problematic because they may cause an infusion pump to display an erroneous volume infused. Additionally, an inaccurate record of total volume infused may result in an inappropriate clinical decision when prescribing further IV therapy. Further, a tube occlusion may delay the administration of critical medications. Delaying the administration of medications to patients may cause complications and may negatively affect the patient's health. For example, delaying the administration of fast-acting drugs (e.g., dopamine, oxytocin, nitroprusside), such as a pain reliever, may cause the patient to experience pain for a longer period of time until the occlusion is remedied. Additionally, delaying the administration of slower-acting drugs, whose effects are not immediately recognized (e.g., heparin, insulin, lidocaine) and may not be realized for several hours, may further delay the effects of the drug. By the time the drug is properly administered, it may take another several hours before the patient receives the benefit of the drug.

The anti-occlusion IV tube port prevents elastomeric IV tube occlusion where a tube exits a pump, and is especially useful in instances when the tube exits at a sharp exit angle. The tube port may include one or more gradually increasing rib to ensure that when an IV tube is bent, it is divided into two or more regions that do not occlude fully, thereby allowing the liquid (e.g., medication) to continue flowing through the tube to the patient. The gradual increase in the rib profile may ensure that the IV tube does not collapse fully, especially when bent sideways or in multiple directions relative to the pump housing. The anti-occlusion IV tube port may also include multiple ribs. For example, multiple ribs strategically spaced on the exterior of the pump housing may advantageously prevent IV tube collapse and occlusion when the tube is bent at various exit angles.

Figure 1A:
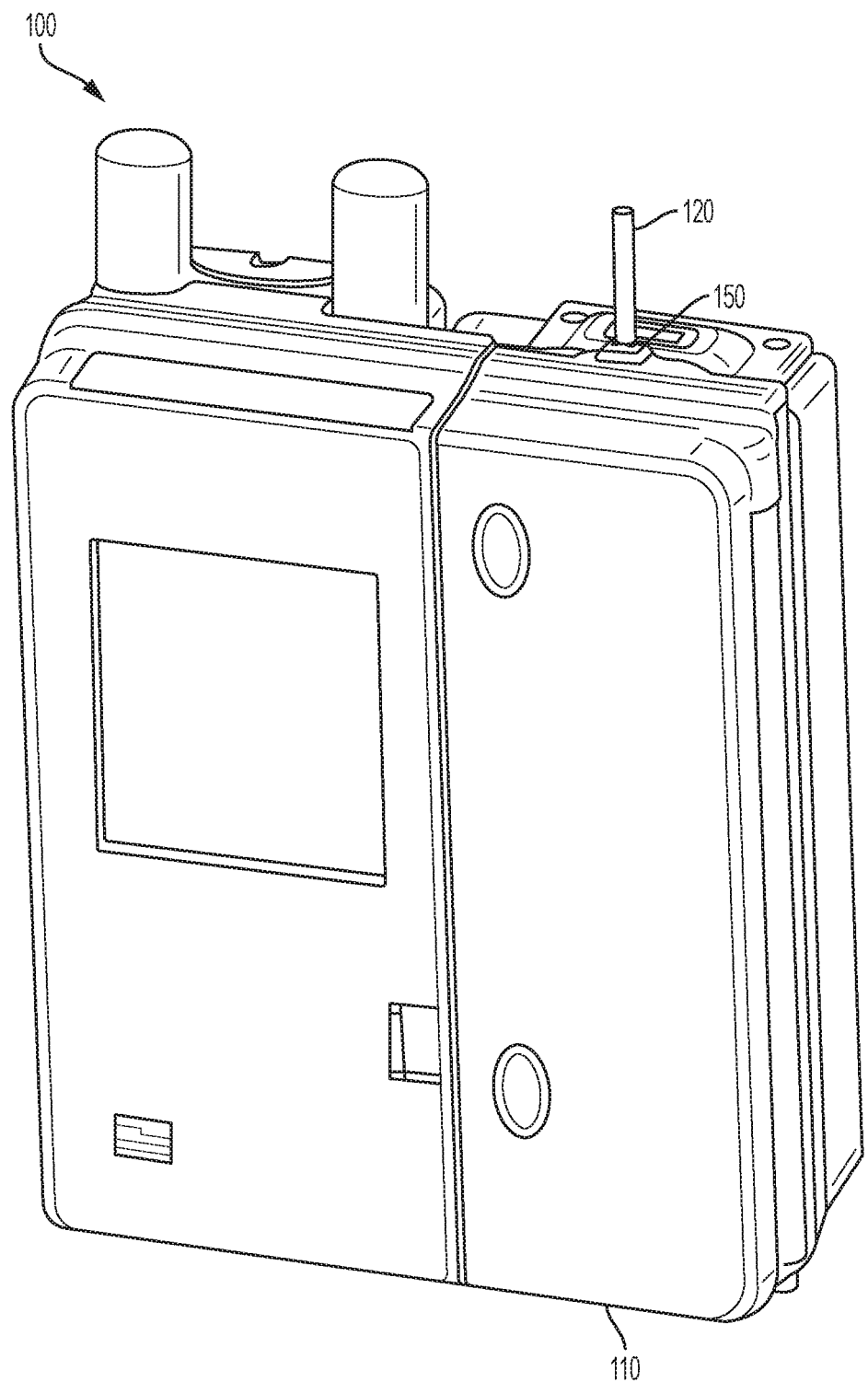
FIG. 1A is an isometric view of an infusion pump according to an example embodiment of the present disclosure.
Figure 1B:
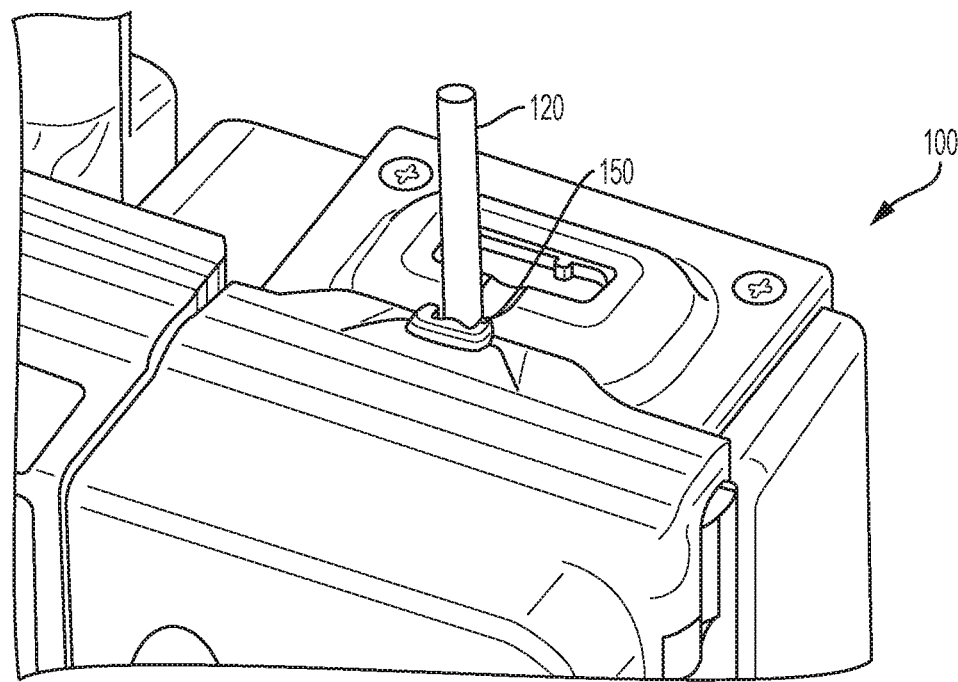
FIGS. 1B and 1C are partial isometric views of an infusion pump according to an example embodiment of the present disclosure.
Figure 1C:
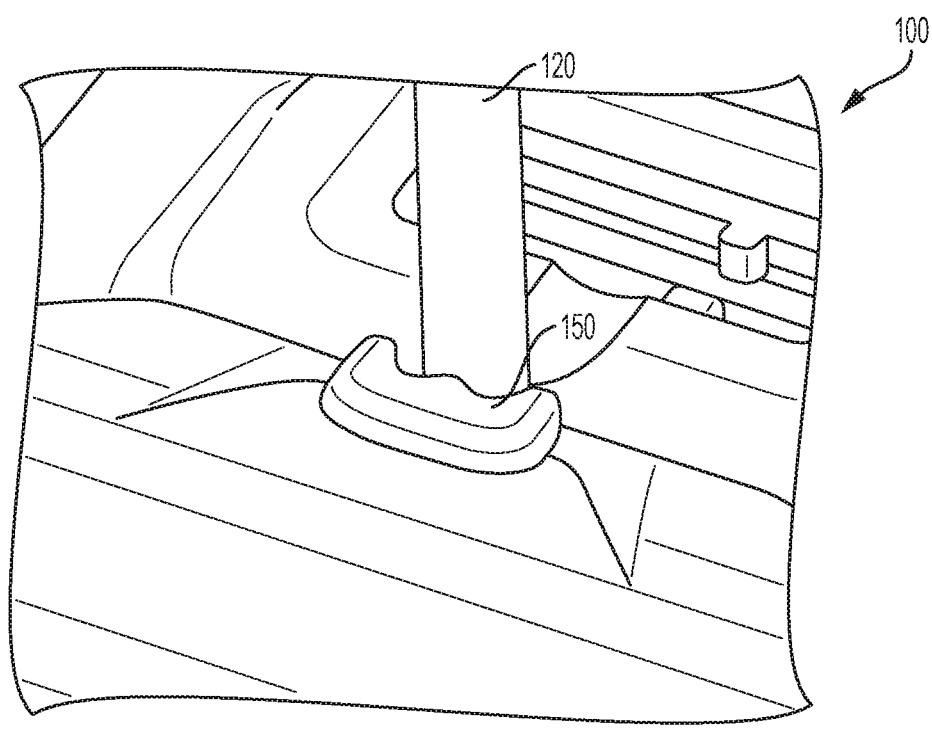
Figure 1D:
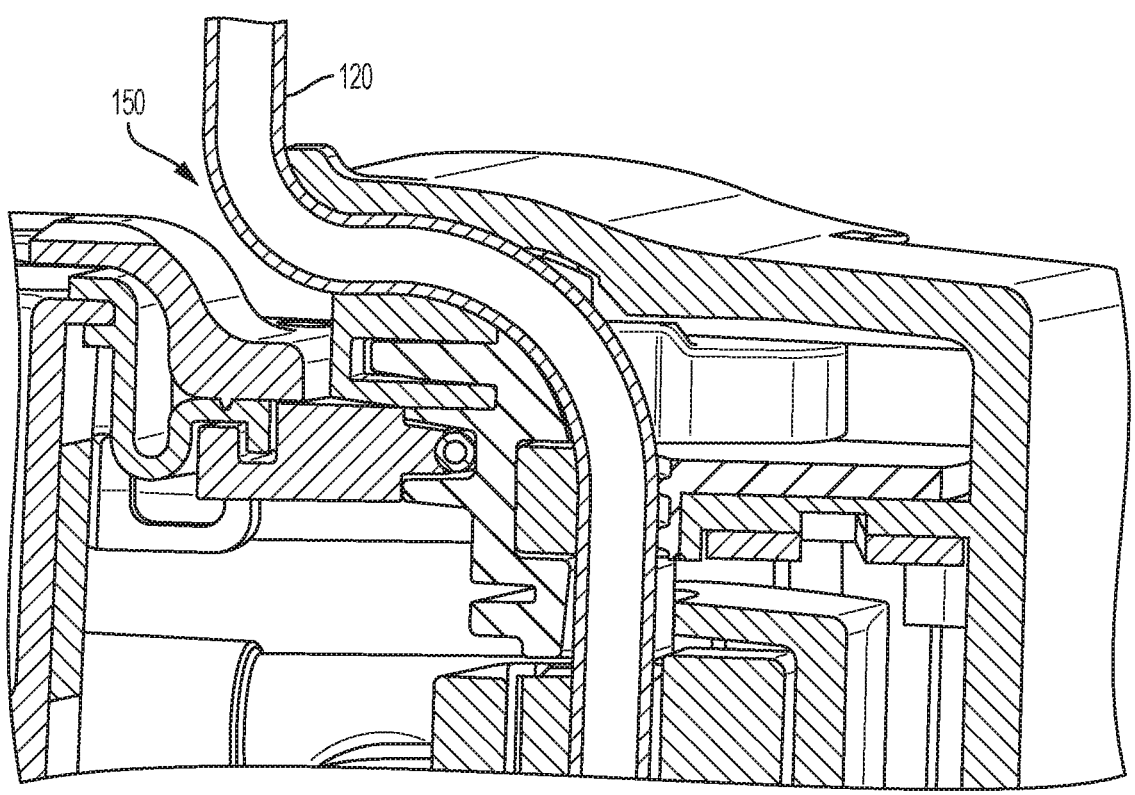
FIG. 1D is a sectional view showing the path of an intravenous ("IV") tube through an infusion pump and exiting a tube port according to an example embodiment of the present disclosure.

Referring to the drawings and in particular to FIGS. 1A to 1D, in one embodiment, an infusion pump 100 of the present disclosure includes a housing 110. All components of pump 100 may be made of metal, plastic, rubber and combinations thereof. Housing 110 may be formed from a single mold or multiple molds and may include a single section or multiple sections that join together to form the housing enclosure 110. For example, housing 110 may include a door that connects to a back portion of the housing 110 to form the pump enclosure. Additionally, housing 110 may include a tube port 150 adapted to receive an IV tube 120. Tube port 150 may extend through a wall of the housing enclosure 110. For example, tube port 150 may extend vertically through a top wall of housing 110 (as illustrated in FIGS. 1A to 1C). In another example, tube port 150 may extend horizontally through a slot or gap in the housing 110 (as illustrated in FIG. 1D, discussed in more detail below). In an embodiment, pump 100 is rotatable as needed so that tube port 150 may extend at virtually any angle.

As illustrated in FIG. 1D, tube 120 may bend and/or take various paths through housing 110. For example, tube 120 may bend to extend along an interior wall of housing 110 before exiting the housing 110 through tube port 150. In another example embodiment, tube 120 may pass through the interior of housing 110 and exit through an opening or slot (e.g., outlet of tube port 150) without bending and/or extending along the interior wall of housing 110. It should be understood that tube 120 may travel along various paths within housing 110 due to different pump configurations and arrangements and that tube port 150 may be configured for each such arrangements.

Figure 2A:
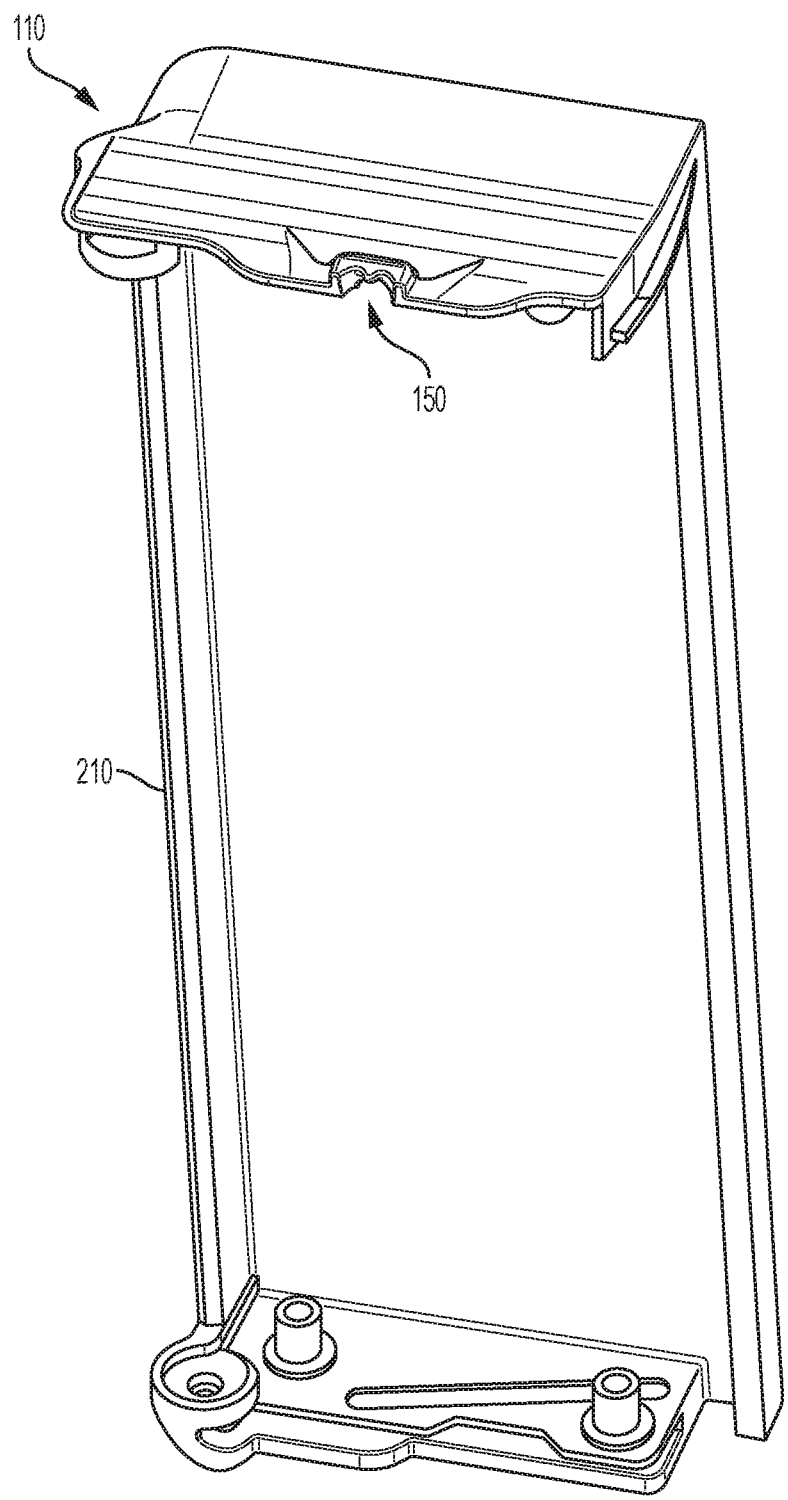
FIG. 2A is an isometric view of a housing for an infusion pump according to an example embodiment of the present disclosure.
Figure 2B:
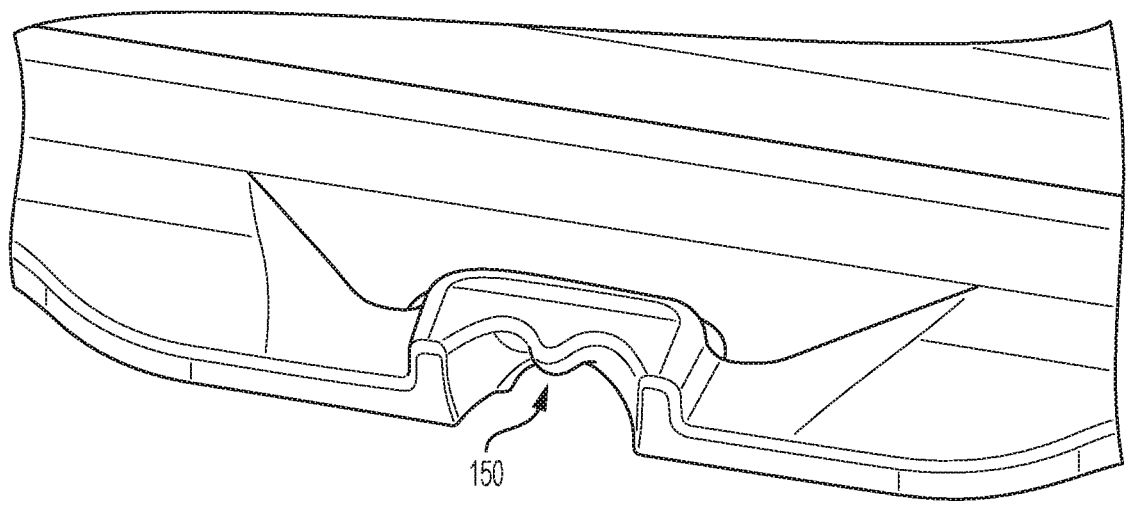
FIGS. 2B and 2C are partial isometric views of a housing for an infusion pump according to an example embodiment of the present disclosure.
Figure 2C:
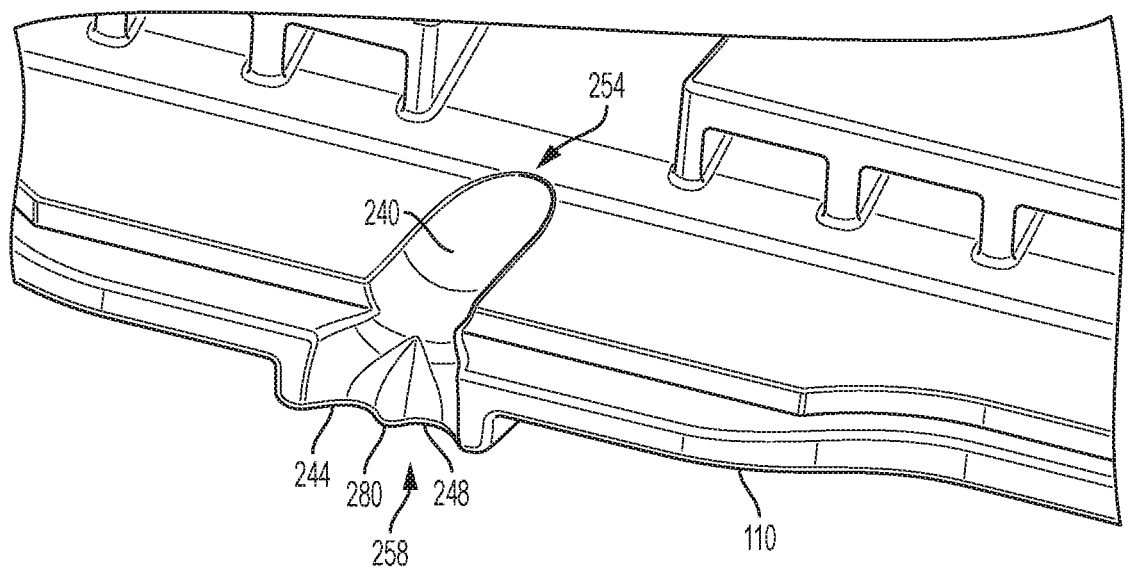

Referring now to FIGS. 2A to 2C, a housing 110 for an infusion pump 100 is illustrated. Housing 110 may include a tube port 150 on a door 210 of the housing enclosure 110. In another example embodiment, tube port 150 may extend through a wall of the housing 110. Additionally, tube port 150 may be positioned at a seam of two joining pieces of housing 110 (e.g., where a door interfaces with a remainder of housing 110). Housing 110 may also include a slit or a gap at which tube port 150 exits.

As illustrated in more detail in FIGS. 2B and 2C, tube port 150 may include a tube channel 240. Tube channel 240, in the illustrated embodiment, has an inlet end 254 and an outlet end 258. For example, tube channel 240 may extend from inlet end 254 to outlet end 258. Additionally, tube channel 240 may have various lengths. For example, the length of tube channel 240 may be configured to adequately provide relief to tube 120. Tube channel 240 may, for example, be long such that tube 120 can more gradually transition as it bends to exit housing 110. In an example embodiment, at inlet end 254, the tube channel 240 may be shallow and may gradually increase in depth as the channel 240 extends towards outlet end 258. For example, a gradually increasing channel depth may advantageously enable tube 120 to bend gradually, thereby reducing stress in the tube and preventing a full collapse of the tube. In another example embodiment, tube channel 240 may have substantially the same depth from inlet end 254 to outlet end 258.

Additionally, tube channel 240 may extend from the interior side of housing 110 to the exterior side of housing 110. For example, tube 120 may extend straight through an aperture or hole (e.g., tube port) in housing 110. In an example embodiment, tube channel 240 may be the inside surface of such an aperture or hole. For example, inlet end 254 and outlet end 258 may be the interior side and exterior side of the aperture or hole through housing 110 respectively. Additionally, tube channel 240 may have a length equal to the thickness of a wall in housing 110.

In a further example embodiment, tube port 250 may include a rib 280 positioned along the channel 240. Rib 280 may extend along various lengths of channel 240. For example, rib 280 may extend along a portion of channel 240. In another example, rib 280 may extend along the entire length of channel 240. Additionally, rib 280 may be located adjacent to outlet end 258 of tube channel 240. Rib 280 may be formed to extend away from channel 240. Additionally, rib 280 may be formed to extend towards an IV tube 120 when the tube 120 is passed through tube port 150. For example, rib 280 may indent tube 120, thereby advantageously preventing full occlusion of tube 120 (described in greater detail below). Rib 280 may indent tube 120 regardless of how tube 120 exits tube port 150 (e.g., regardless of exit angle, pull force, direction, etc.). In an example embodiment, rib 280 may indent tube 120 when tube 120 is bent or pulled in a specific direction. Additionally, rib 280 may split tube channel 240 into a first channel 244 and a second channel 248. As rib 280 partially deforms tube 120, tube 120 may fit into first and second channels 244, 248, which are configured to provide adequate space for regions of tube 120 to remain open and prevent fully occluding tube 120. In an example, first and second channels 244, 248 may be symmetrical. For example, rib 280 may be positioned along a center-line of channel 240. In another example embodiment, first and second channels 244, 248 may asymmetrical. For example, first and second channels 244, 248 may have a different profiles and/or different shapes. Additionally, rib 280 may be offset from a center-line of tube channel 240, thereby creating asymmetrical first and second channels 244, 248.

In another example embodiment, multiple ribs 280 may be positioned along channel 240. For example, there may exist two ribs positioned along channel 240 in an in-line arrangement. In another example embodiment, there may be more than two ribs 280 positioned in an in-line arrangement. Additionally, multiple ribs 280 may be positioned side-by-side or be offset from the center-line of tube channel 140. In such an embodiment, the ribs 280 may split tube channel 240 into two or more channels into which tube 120 fits.

Figure 3:
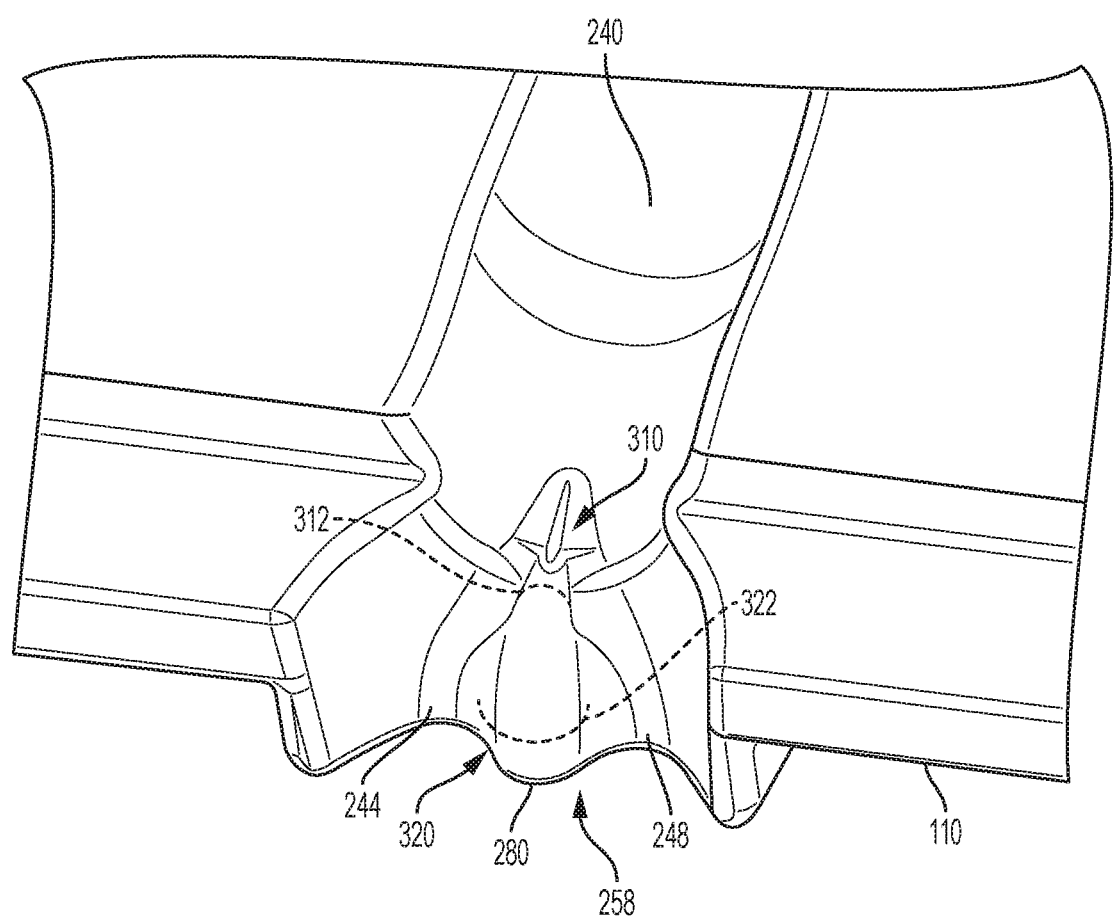
FIG. 3 is an isometric view of a tube port according to an example embodiment of the present disclosure.

Referring now to FIG. 3, rib 280 may include a first end 310 and second end 320. Second end 320 may be closer to an outside opening of the tube port 250 than the first end 310. At first end 310, rib 280 may have a low profile similar to channel 240, and as the rib extends towards the second end 320, rib 280 may have a large profile (e.g., taller and wider than profile at first end 310). In an example embodiment, the first end 310 of rib 280 may start at the inlet end 254 of tube channel 240. In another example, first end 310 may start somewhere between inlet end 254 and outlet end 258 of tube channel 240. For example, rib 280 may have a first end 310 that starts at a half-way point of channel 240 and may extend along the second half of channel 240. In other example, rib 280 may extend along a third of the length of the tube channel 240. In addition, the second end 320 of rib 280 may be located at the outlet end 258 of tube channel 240. In another example embodiment, second end 320 may be positioned before the outlet end 258.

In an example embodiment, rib 280 may have a rounded profile and may gradually increase as it extends along tube channel 240 towards outlet end 258. For example, first end 310 may have a first diameter 312 and second end 320 may have a second diameter 322. In an example, first and second diameters 312, 322 may be different. Additionally, second diameter 322 may be larger than first diameter 312, such that the profile of rib 280 increases (e.g., is taller and/or wider) at the second end 320 near outlet end 258 of tube port 150. A gradually increasing rib 280 advantageously ensures that when an IV tube 120 is bent, tube 120 is gradually divided into two regions that do not collapse, thereby preventing a full occlusion of the tube (as illustrated in FIGS. 17A to 18C, described in more detail below).

Rib 280 may include a rounded profile such that it forms (or helps to form) a rounded "W" shape with tube channel 240 as illustrated for example in FIG. 3. For example, first and second channels 244 and 248 may reside in the valleys of the rounded "W", while rib 280 forms the peak in the middle of the rounded "W". If the profile of rib 280 gradually increases, the peak of the rounded "W" may gradually become higher and wider as rib 280 extends towards outlet end 258 of tube channel 240. Rib 280 may be positioned and arranged such that it indents the tube 120, which advantageously tends to prevent full occlusion of tube 120. For example, a gradually increasing profile may advantageously ensure that when tube 120 is bent, it is divided into two regions that do not fully collapse, thereby preventing a full occlusion of tube 120.

Figure 4A:
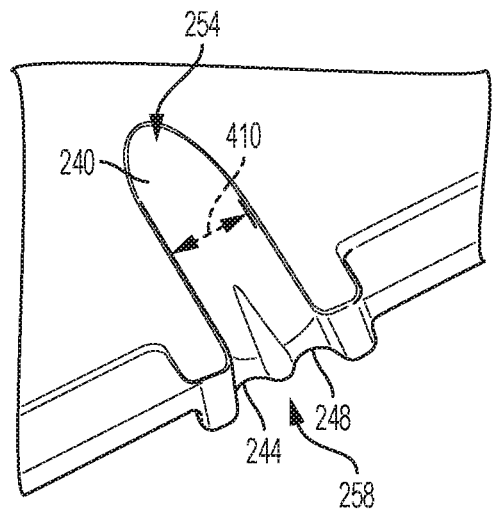
FIGS. 4A to 4D are isometric views of a tube port according to various example embodiments of the present disclosure.
Figure 4B:
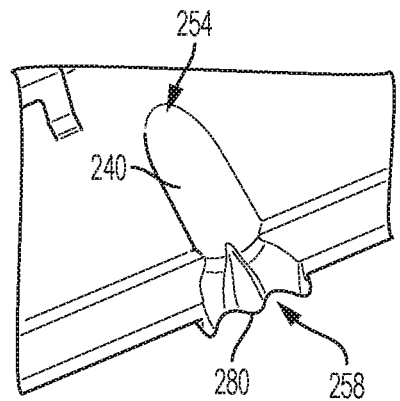
Figure 4C:
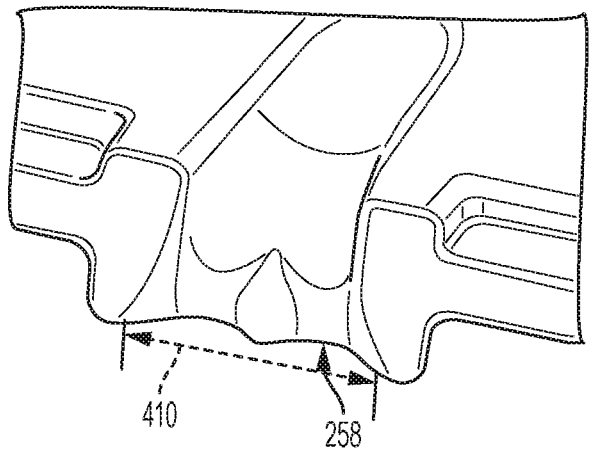
Figure 4D:
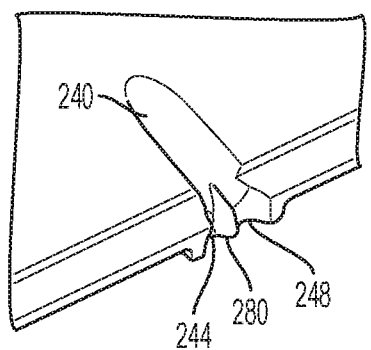
Figure 5A:
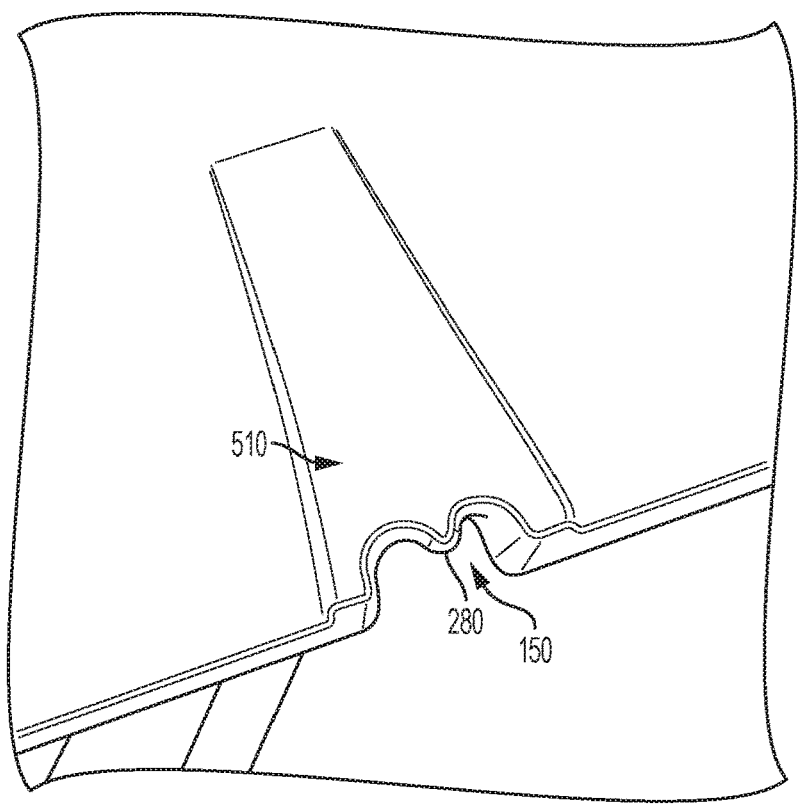
FIG. 5A is a top view of a tube port according to an example embodiment of the present disclosure.
Figure 5B:
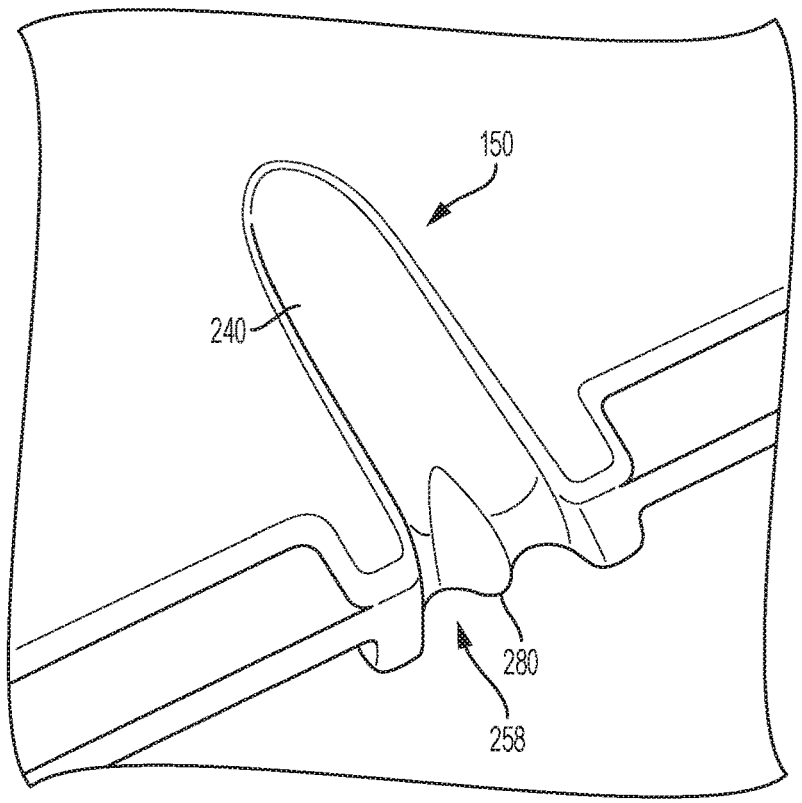
FIG. 5B is a bottom view of a tube port according to an example embodiment of the present disclosure.
Figure 6A:
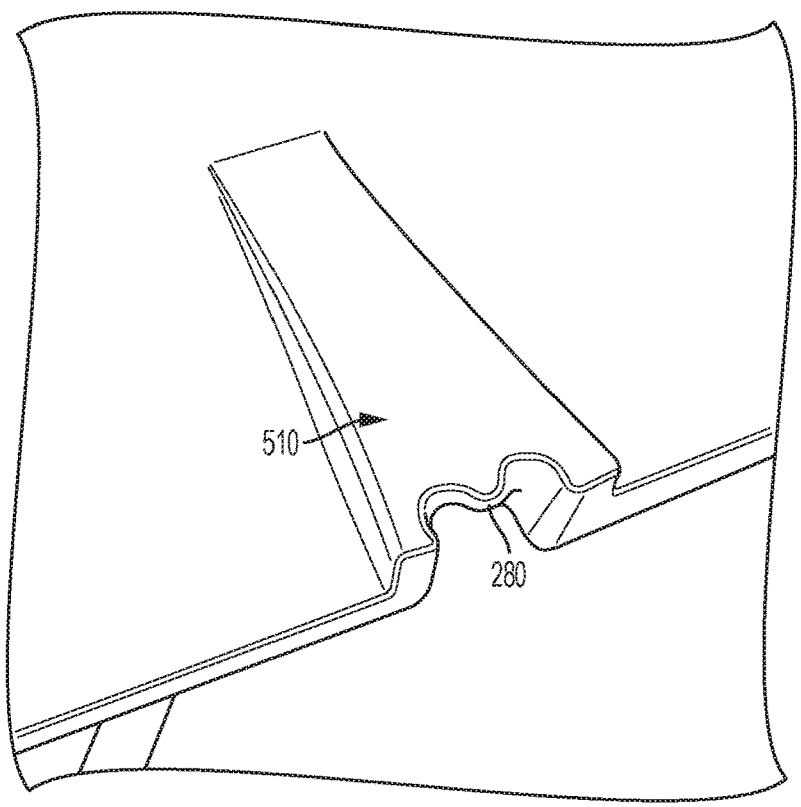
FIG. 6A is a top view of a tube port according to an example embodiment of the present disclosure.
Figure 6B:
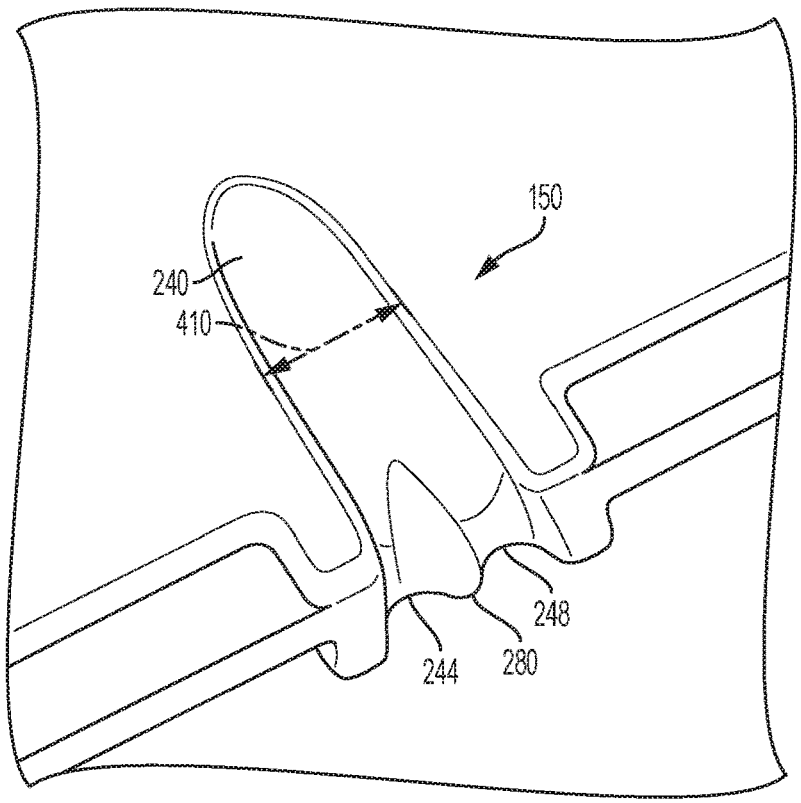
FIG. 6B is a bottom view of a tube port according to an example embodiment of the present disclosure.
Figure 7A:
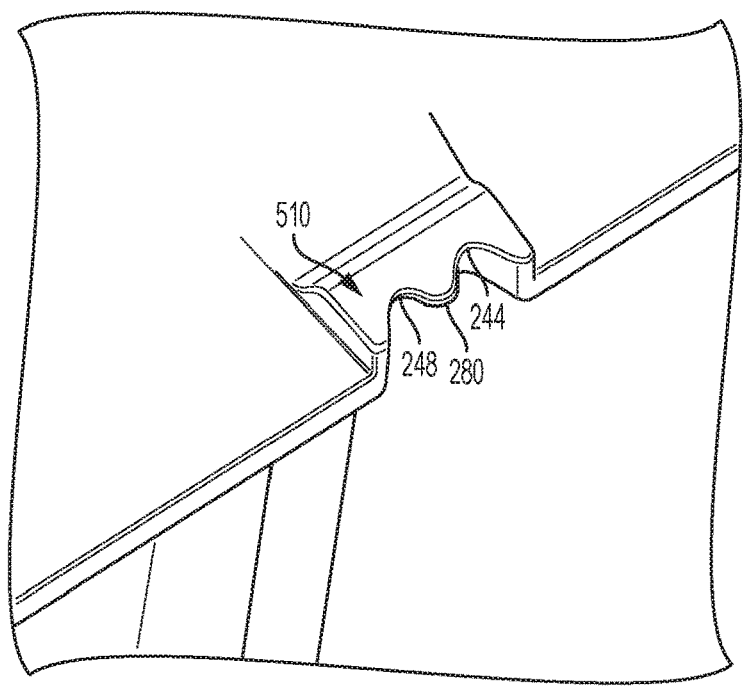
FIG. 7A is a top view of a tube port according to an example embodiment of the present disclosure.
Figure 7B:
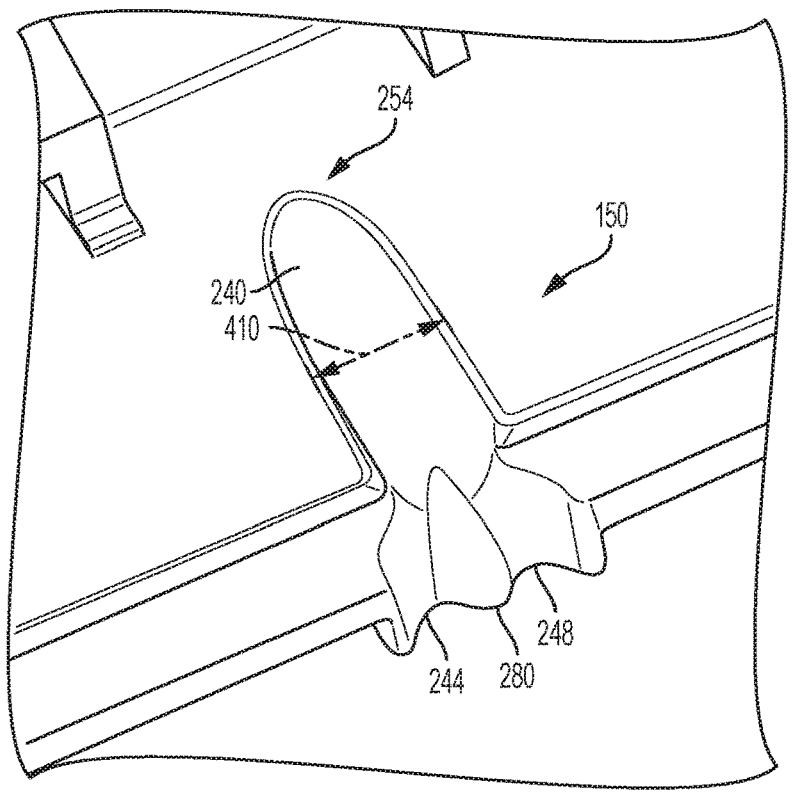
FIG. 7B is a bottom view of a tube port according to an example embodiment of the present disclosure.
Figure 8A:
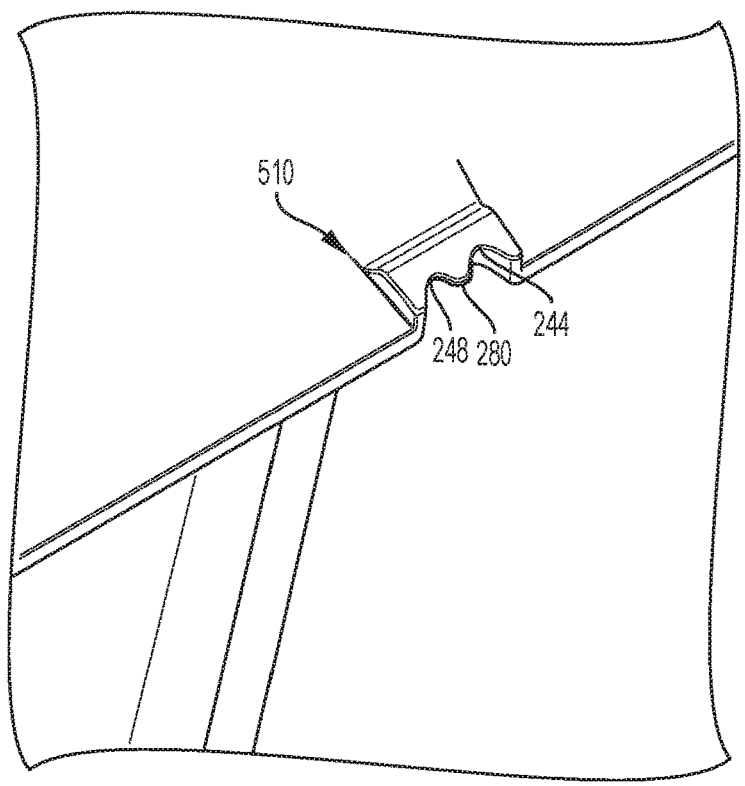
FIG. 8A is a top view of a tube port according to an example embodiment of the present disclosure.
Figure 8B:
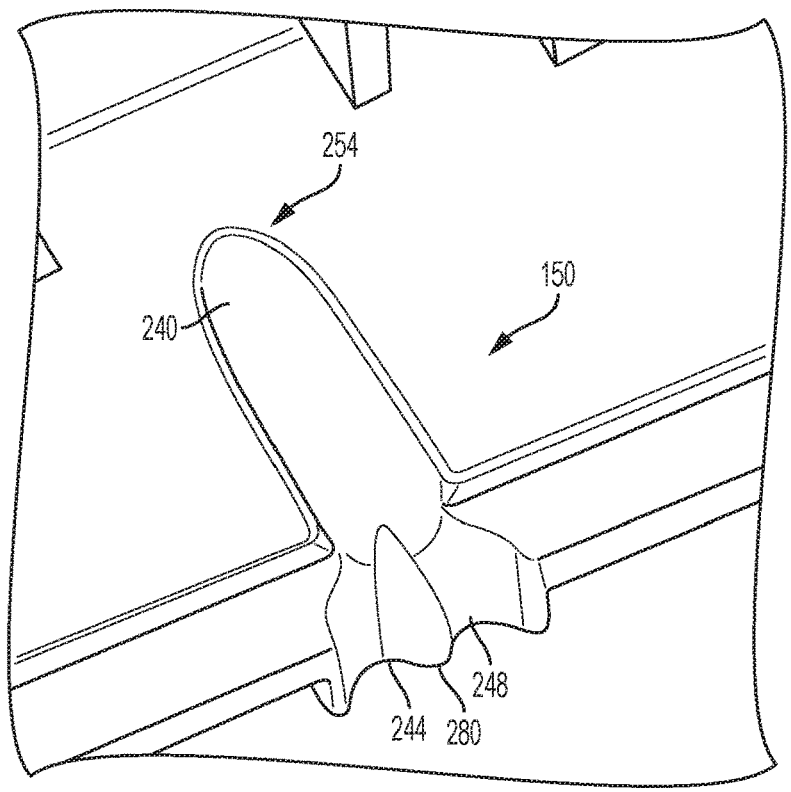
FIG. 8B is a bottom view of a tube port according to an example embodiment of the present disclosure.
Figure 9A:
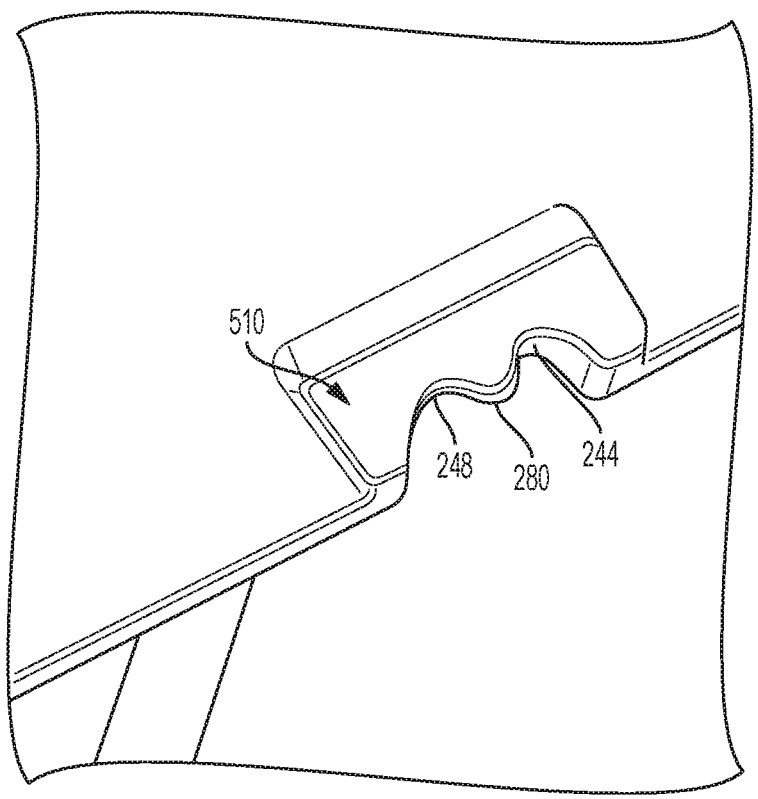
FIG. 9A is a top view of a tube port according to an example embodiment of the present disclosure.
Figure 9B:
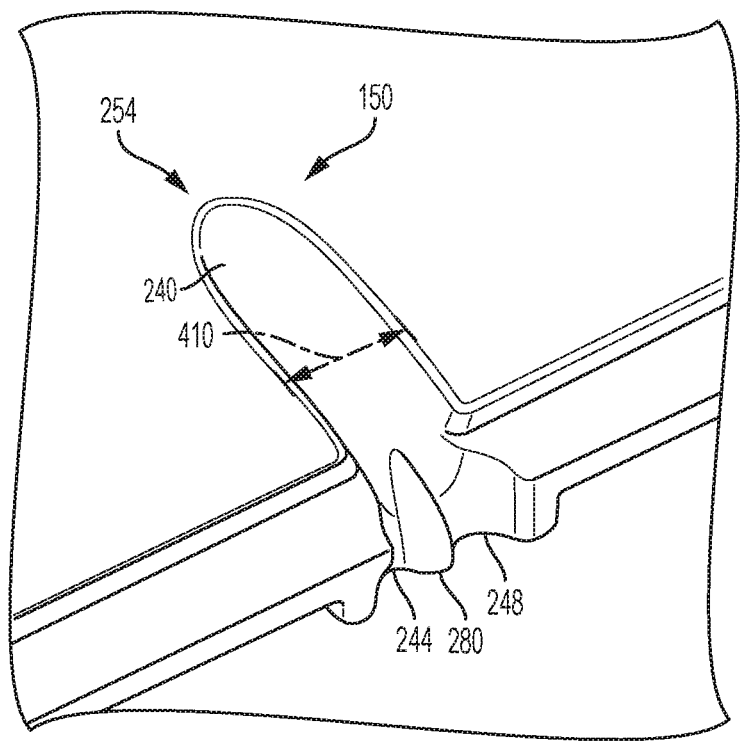
FIG. 9B is a bottom view of a tube port according to an example embodiment of the present disclosure.
Figure 10A:
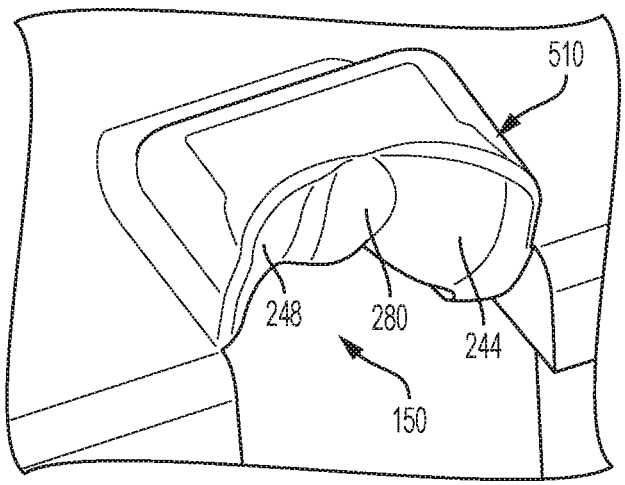
FIG. 10A is a top view of a tube port according to an example embodiment of the present disclosure.
Figure 10B:
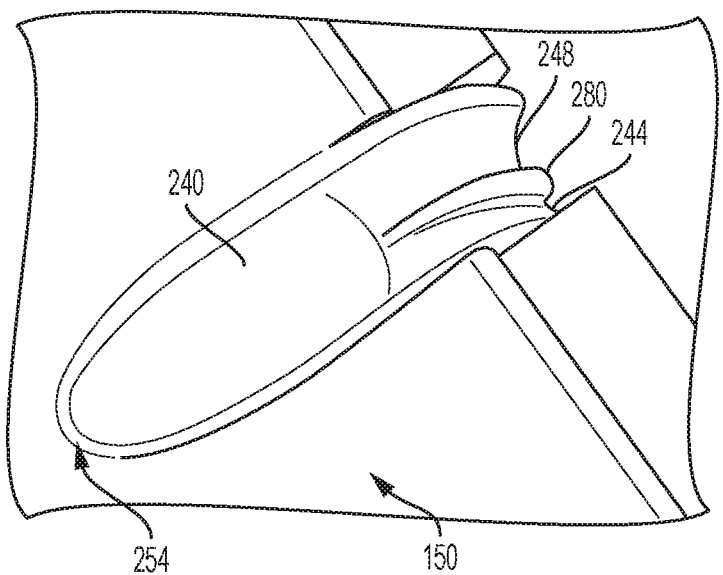
FIG. 10B is a bottom view of a tube port according to an example embodiment of the present disclosure.
Figure 10C:
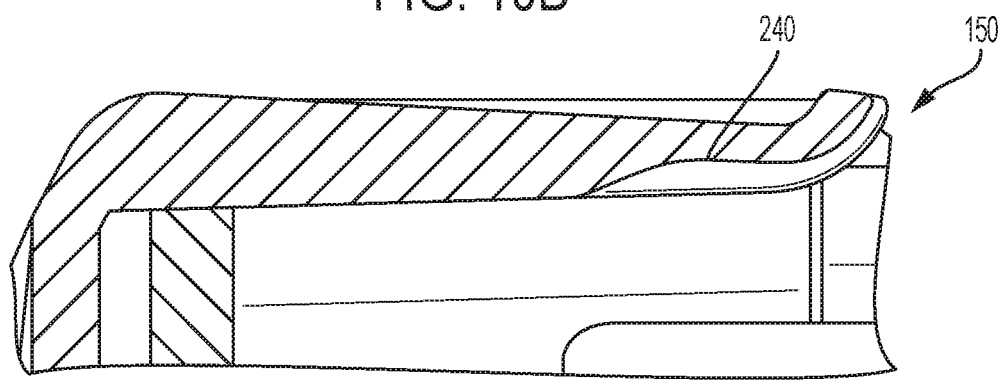
FIG. 10C is a sectioned view of a tube port according to an example embodiment of the present disclosure.

FIGS. 4A to 4D illustrate various other example embodiments of tube ports 150. For example, as illustrated in FIG. 4A, tube channel 240 may have a substantially similar channel width 410 from inlet end 254 to outlet end 258. In another example embodiment, tube channel 240 may have a variable channel width 410. For example, as illustrated in FIGS. 4B to 4D, channel width 410 may be larger at outlet end 258 than at inlet end 254. In an example, channel width 410 may be larger than an outside diameter of tube 120. In another example, channel width 410 may be substantially similar to the outside diameter of tube 120. Additionally, channel width 410 may be configured to provide extra support to tube 120 to prevent tube 120 from fully flattening during a bend and becoming fully occluded. Further additionally, channel width 410 may be greater at outlet end 258 to provide sufficient space as tube 120 bends and deforms (e.g., thereby creating a wider profile of tube 120) over rib 280.

FIGS. 5A to 10C illustrate other example embodiments of tube ports 150. For example, tube channel 240 may be positioned along an interior wall of housing 110 such that tube channel 240 is substantially perpendicular to the exit of tube port 150. For example, a tube 120 passing through the tube port 150 may be seated in tube channel 240 along an interior wall of housing 110 and may turn at least substantially 90 degrees before exiting housing 110 (see e.g., FIG. 1D). In other example embodiments, tube 120 may exit housing 110 at various exit angles. In an example embodiment, the length of tube channel 240 may be extended by including a ridge 510 on housing 110 through which tube 120 passes. Ridge 510 may be provided to ensure housing 110 has sufficient thickness to support a channel 240 with adequate depth without reducing the structural integrity of housing 110. Ridge 510 may advantageously provide additional support to housing 110 in areas where tubes 120 exit housing 110. For example, in some cases, a tube 120 may exit by turning sharply from infusion pump 100, which may add additional stress to tube 120 and housing 110. Ridge 510 enables the tube channel 240 and associated rib 280 to increase in length, thereby advantageously allowing tube 120 more space to transition through the bend without collapsing.

Ridge 510 may have various shapes and sizes (e.g., width, height, etc.). In an example, ridge 510 may extend along an exterior side of housing 110, e.g., along the length of tube channel 240 (as illustrated in FIGS. 5A to 6B). In another example, ridge 510 may be positioned primarily near outlet end 258 of tube channel 240, as illustrated in FIGS. 7A to 10B.

Figure 11A:
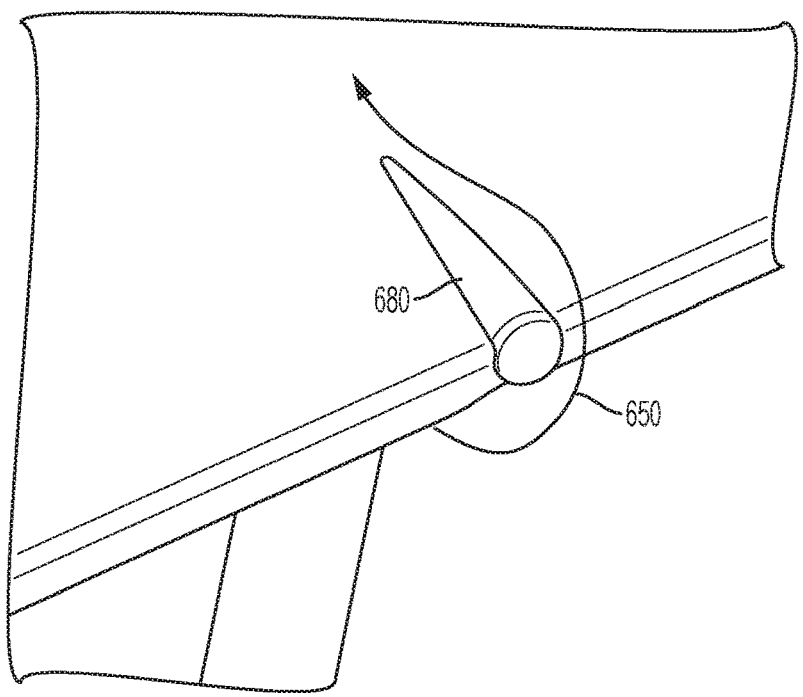
FIG. 11A is a top view of a tube port according to an example embodiment of the present disclosure.
Figure 11B:
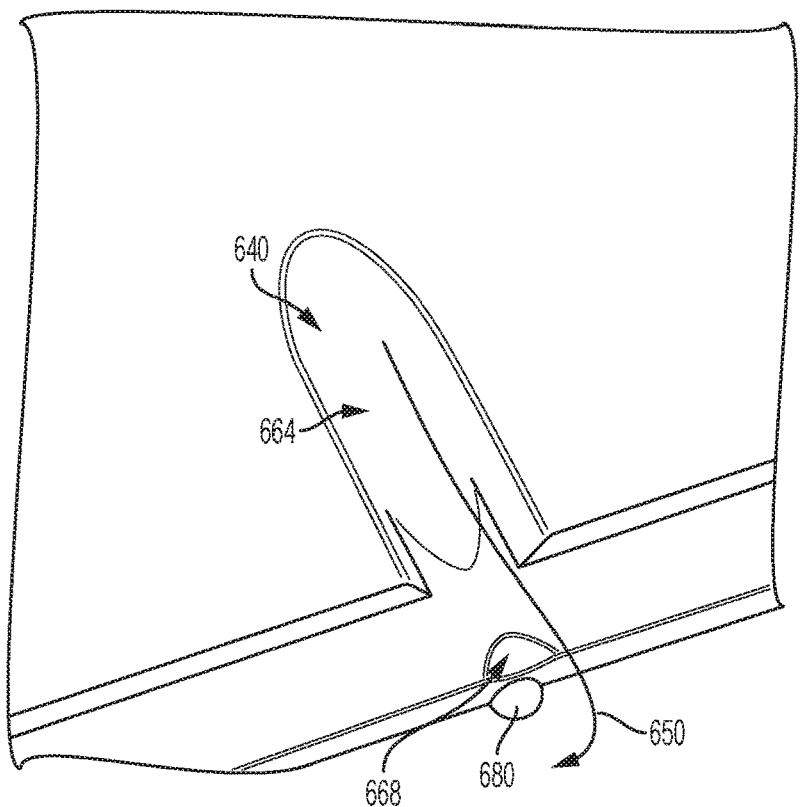
FIG. 11B is a bottom view of a tube port according to an example embodiment of the present disclosure.
Figure 12A:
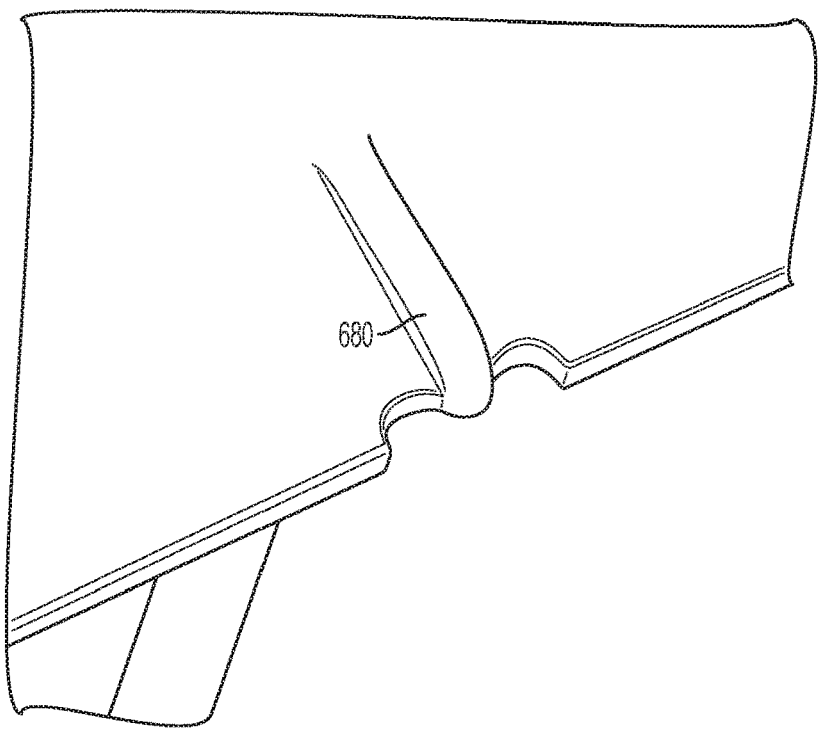
FIG. 12A is a top view of a tube port according to an example embodiment of the present disclosure.
Figure 12B:
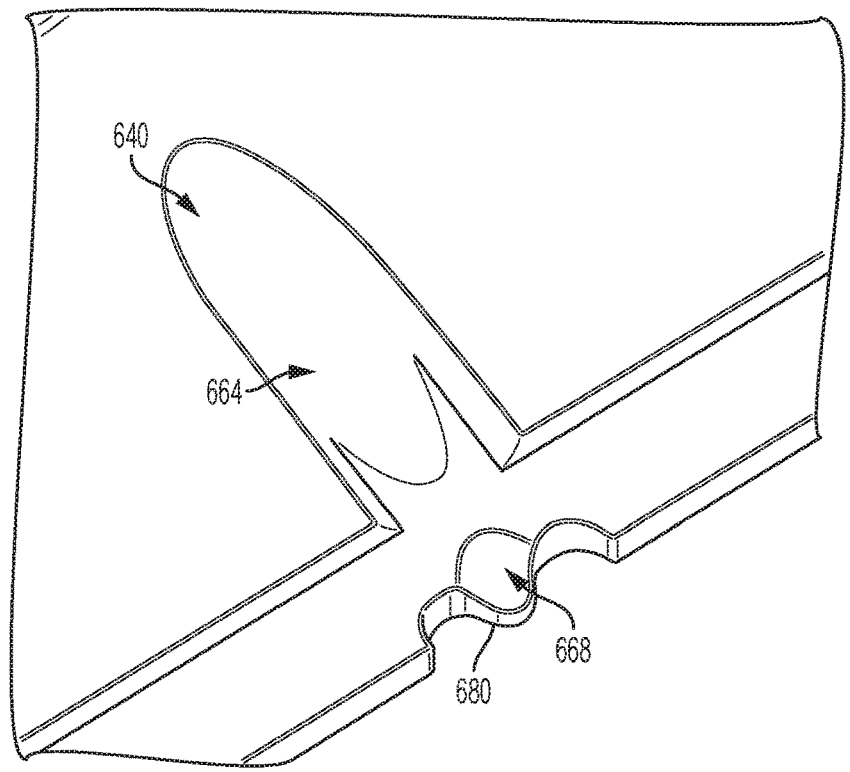
FIG. 12B is a bottom view of a tube port according to an example embodiment of the present disclosure.
Figure 13A:
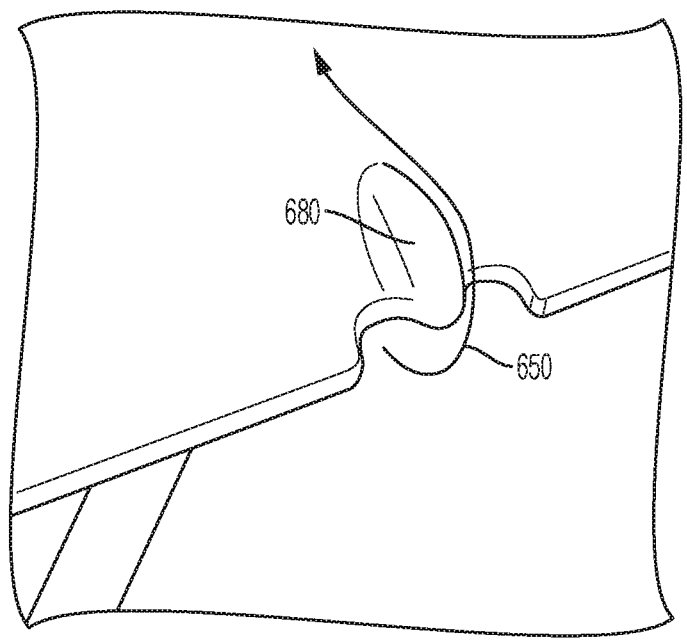
FIG. 13A is a top view of a tube port according to an example embodiment of the present disclosure.
Figure 13B:
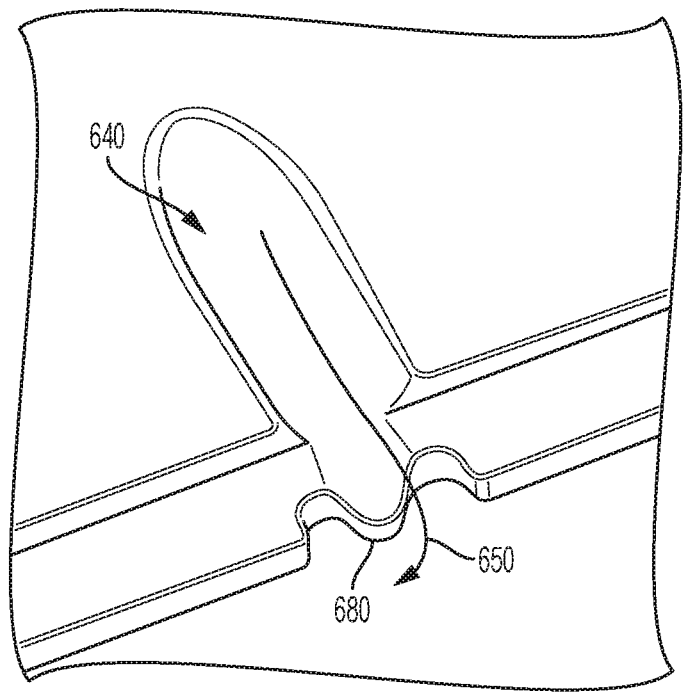
FIG. 13B is a bottom view of a tube port according to an example embodiment of the present disclosure.

Referring now to FIGS. 11A to 13B, tube port 150 may include a rib 680 positioned on the exterior side of housing 110. For example, as tube 120 is bent towards rib 680, rib 680 may selectively indent tube 120 to prevent full occlusion of the tube. As illustrated in FIGS. 11A and 11B, rib 680 may be suited for scenarios in which tube 120 exits housing 110 and extends along the exterior of the housing 110. For example, as tube 120 extends along path 650 (indicated by the arrow), rib 680 may advantageously divide tube 120 into two un-occluded regions. As illustrated in the FIGS. 11B and 12B, tube channel 640 may have two separate regions (e.g., first region 664 and second region 668) to aid tube 120 in gradually curling over the edge of housing 110. For example, tube 120 may be seated in tube channel 640 and may start to curve away from housing 110 before gradually curling back towards housing 110 and around rib 680. FIGS. 12A to 13B illustrate other configurations of rib 680 and tube channel 640.

Figure 14A:
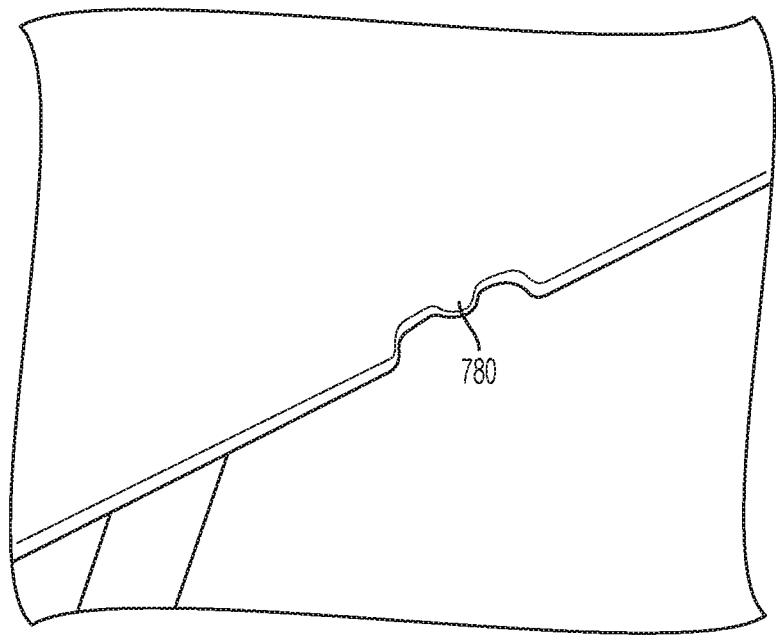
FIG. 14A is a top view of a tube port according to an example embodiment of the present disclosure.
Figure 14B:
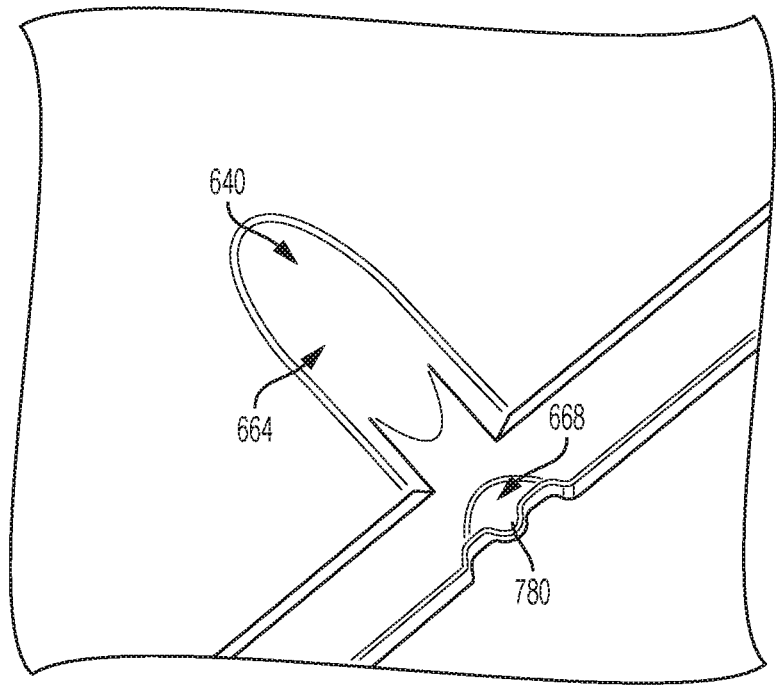
FIG. 14B is a bottom view of a tube port according to an example embodiment of the present disclosure.

Referring now to FIGS. 14A and 14B, tube port 150 may include or form rib 780. In an example embodiment, rib 780 may not extend along the tube channel, but may instead be positioned at the outlet end 258 of the tube channel 240. For example, rib 780 may be positioned on an edge of a portion of housing 110 where two portions of housing 110 meet (e.g., edge of a door that mates with a remainder of housing enclosure). In an example embodiment, rib 780 may create a "W" shaped profile in the exit aperture (e.g., outlet end 258 of tube channel 240) of housing 110. As tube 120 extends through the exit aperture, rib 280 advantageously divides tube 120 into two regions that do not fully collapse, thereby preventing a full occlusion in tube 120.

Figure 16:
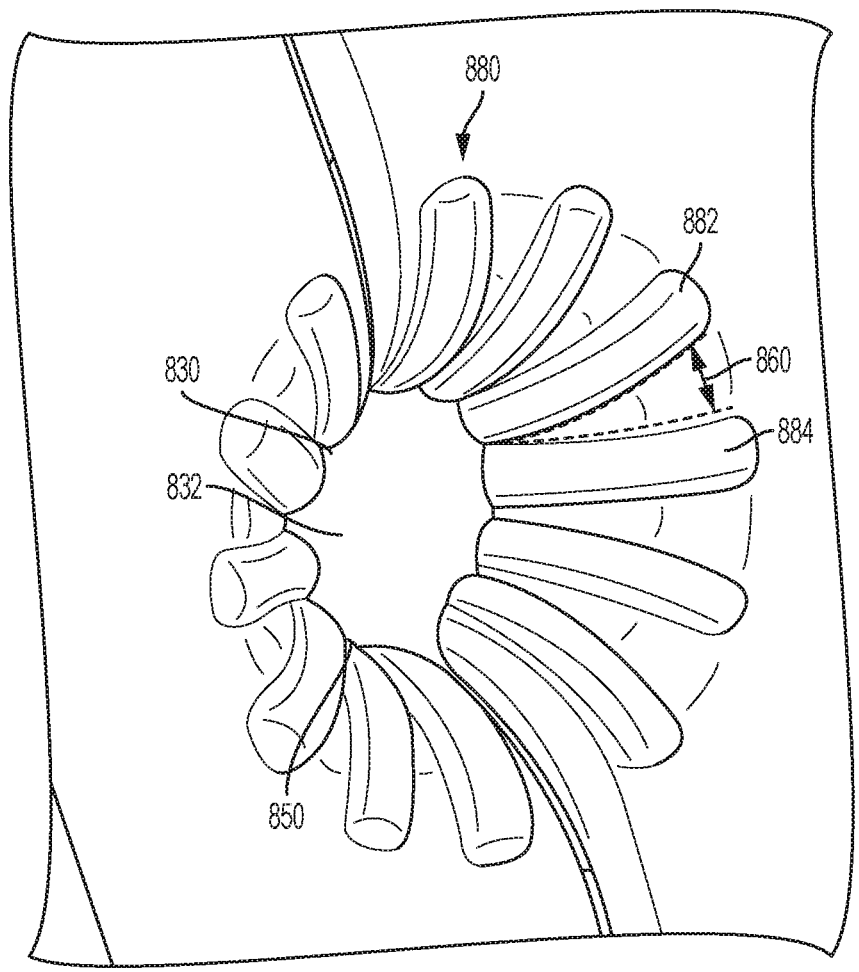
FIG. 16 is an isometric view of a tube port according to an example embodiment of the present disclosure.

Referring now to FIGS. 15 and 16, a housing 110 may include a tube port 850 extending through one of its walls. In an example embodiment, tube port 850 is configured to receive an IV tube 120. Additionally, tube port 850 may include a plurality of ribs 880. The plurality of ribs 880 may be positioned around a perimeter 830 of tube port 850, e.g., on the exterior side of housing 110. For example, the plurality of ribs 880 may be circumferentially positioned around perimeter 830 (spaced apart evenly or not evenly as desired). In the illustrated embodiment, each rib of the plurality of ribs 880 may extend radially towards a center 832 of tube port 850. Ribs 880 may alternatively extend non-radially with respect to center 832 of tube port 850.

As illustrated in FIG. 16, each rib may have approximately the same size and shape. For example, a first rib 882 of the plurality of ribs 880 and a second rib 884 of the plurality of ribs 880 may both have a cylindrical shape. In an example embodiment, the first and second ribs 882, 884 may have a different sizes and/or shapes (e.g., differing height, length, and/or profile, etc.). For example, the plurality of ribs 880 may include two different rib profiles that alternate as the plural ribs 880 are positioned around a perimeter 830 of tube port 850. Specifically, as the plural ribs 880 are positioned about perimeter 830, they may be patterned such that every other rib has a different profile (e.g., profile A, profile B, profile A, . . . , etc.).

In an example embodiment, spacing between each rib in the plurality of ribs 880 may gradually decrease as the ribs 880 approach the tube port 850. For example, first rib 882 and second rib 884 may be separated by a rib spacing 860. In another example embodiment, rib spacing 860 may remain substantially constant between the ribs. Additionally, ribs 880 may be shaped (e.g., height, width, profile, etc.) based on dimensions of tube 120. For example, ribs 880 may be configured and arranged such that the rib spacing 860, profile of the ribs 880, etc., prevent full occlusions in tube 120 regardless of the tube exit angle from the associated pump housing.

Figure 17A:
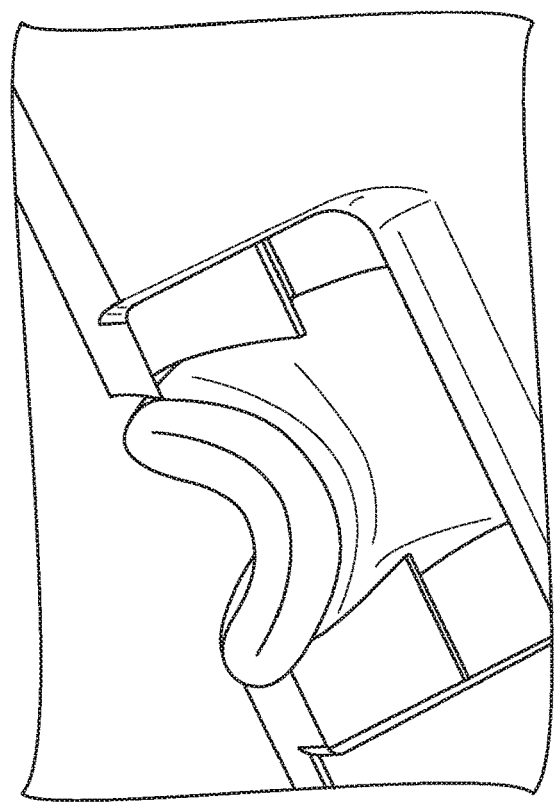
FIG. 17A is a view of an example fully collapsed and occluded tube extending out of a conventional tube opening.
Figure 17B:
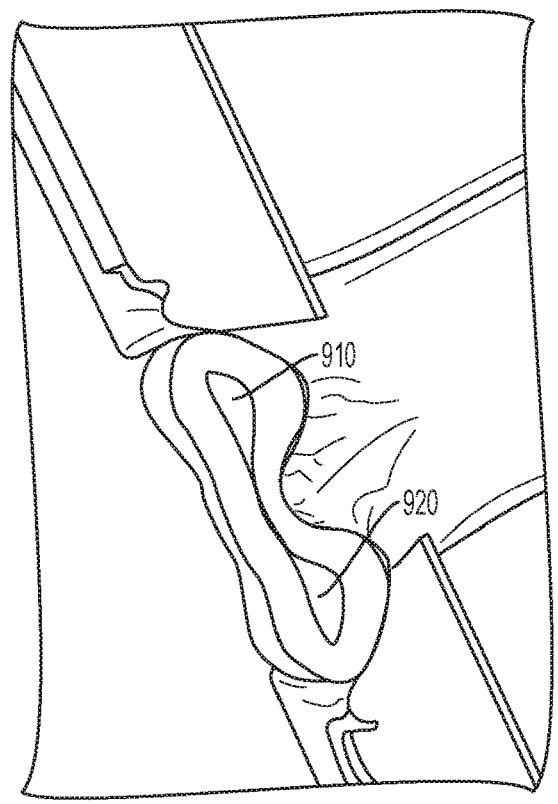
FIG. 17B is a view of a non-occluded tube extending out of a tube port according to an example embodiment of the present disclosure.

Referring now to FIGS. 17A and 17B, tube 120 is shown exiting a housing without the anti-occlusion features of the present disclosure (as illustrated in FIG. 17A) and alternatively with an anti-occlusion feature (e.g., rib 280) of the present disclosure (as illustrated in FIG. 17B). As illustrated in FIG. 17A, tube 120 collapses under tension due to excessive stress on the tube wall caused by the tube 120 being bent upon exiting the housing. Alternatively, FIG. 17B shows that housing 110 includes tube port 150 having a gradually increasing rib (e.g., rib 280). As illustrated, the gradually increasing rib (e.g., rib 280) ensures that when the tube 120 is bent, if the tube is occluded, tube 120 is divided into two regions (e.g., first region 910 and second region 920) that do not fully collapse or occlude, which allows for the liquid (e.g., drug or medication) to continue flowing through tube 120. Additionally, rib 280 causes the middle of tube 120 to gradually compress and form two regions (e.g., first and second regions 910, 920) at first and second channels 244, 248, which allow the liquid to continue flowing through tube 120. Further additionally, first and second channels 244, 248 of tube channel 240 provide tube 120 sufficient room to conform around rib 280 and create first and second regions 910, 920.

Figure 18A:
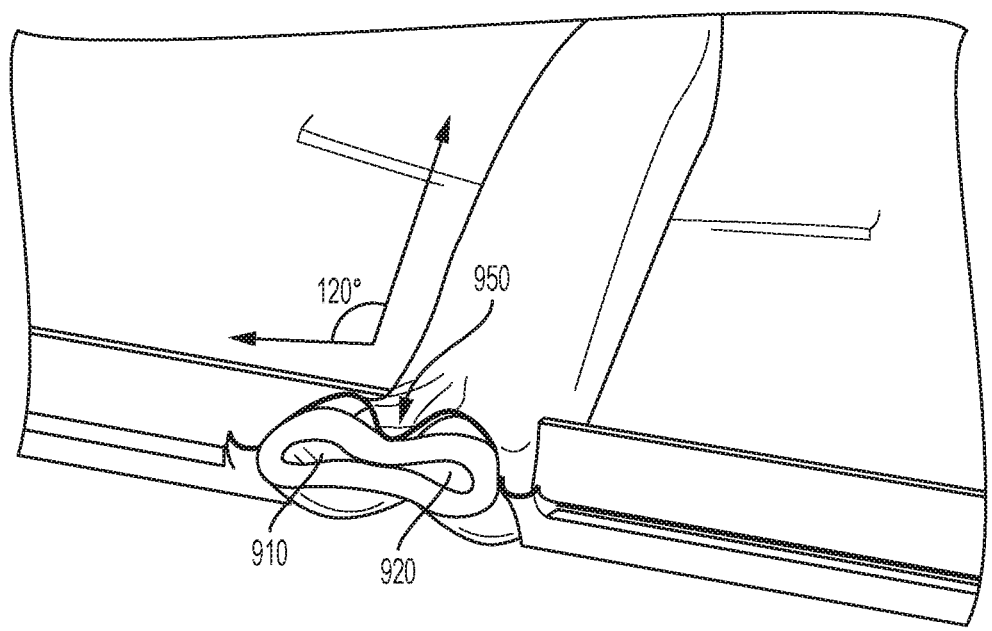
FIGS. 18A and 18B are views of a non-occluded tube extending out of a tube port according to an example embodiment of the present disclosure.
Figure 18B:
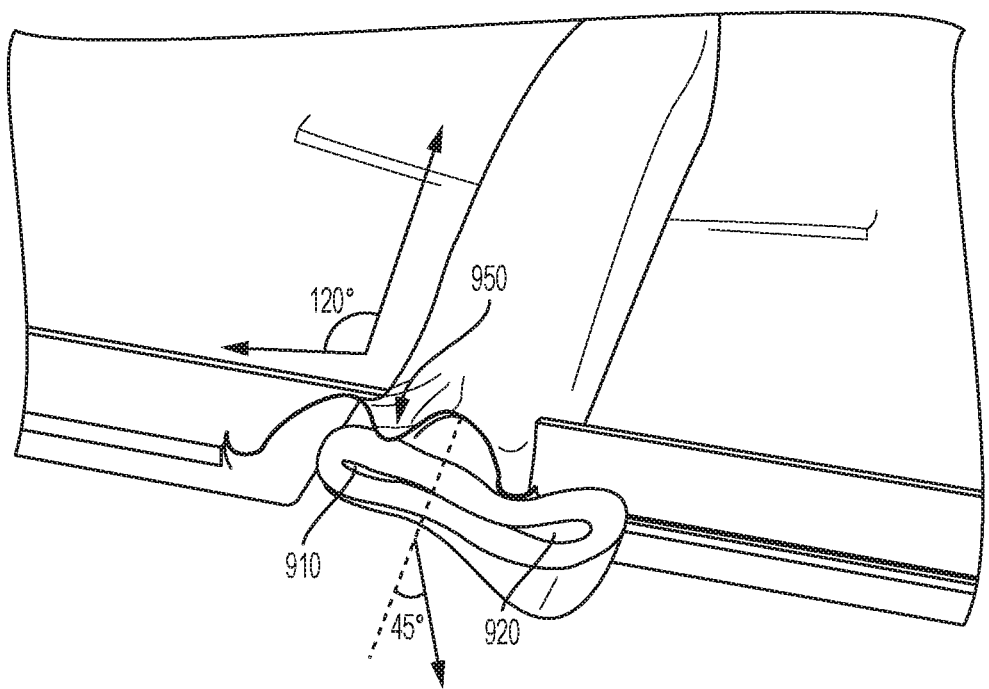
Figure 18C:
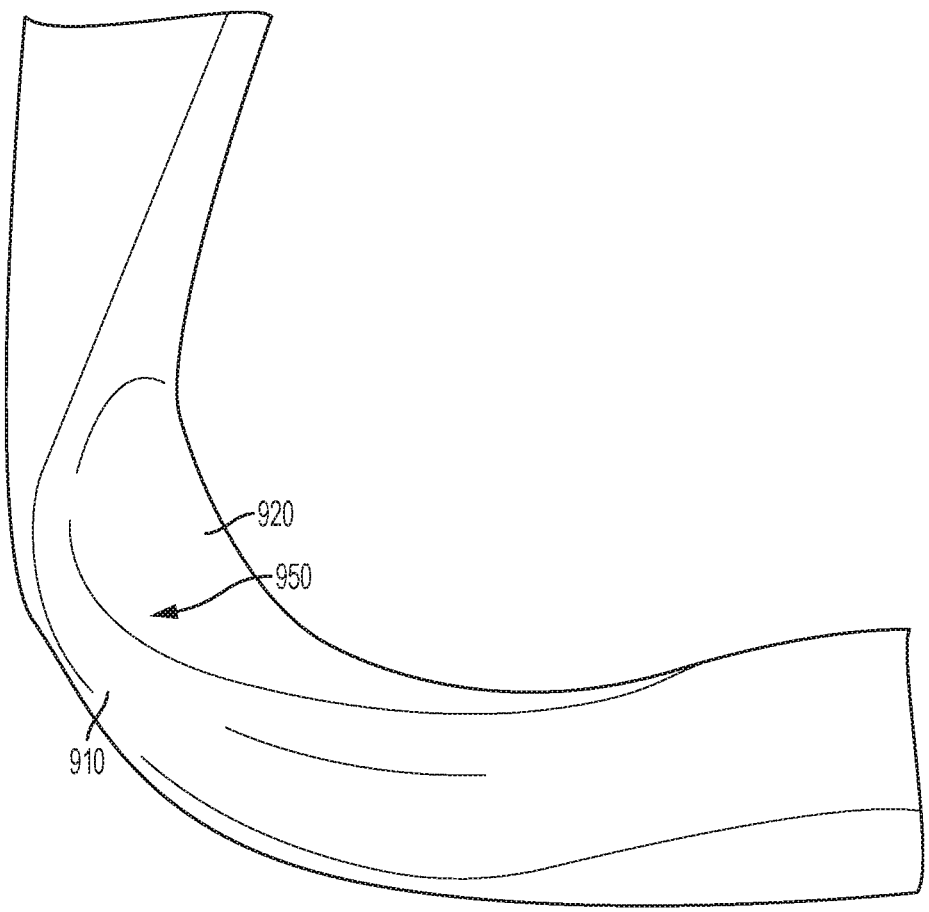
FIG. 18C illustrates an intravenous tube deformed over a rib in a tube port according to an example embodiment of the present disclosure.

Referring now to FIGS. 18A to 18C, tube 120 is shown (i) exiting housing 110 at a one-hundred twenty degree angle towards the back of the housing (e.g., from a plane parallel to the interior side of housing 110 as illustrated in FIG. 18A) and (ii) exiting housing 110 at a one-hundred twenty degree angle towards the back of the housing and 45 degrees to the side (as illustrated in FIG. 18B). Additionally, FIG. 18C illustrates an IV tube 120 deformed over an anti-occlusion feature such as rib 280. Tube 120 in each of FIGS. 18A to 18C includes a deformed area 950 that is divided into two regions that do not fully collapse (e.g., first and second regions 910, 920). As discussed above, the gradually increasing rib profile ensures that when an IV tube is bent, it does not fully or abruptly collapse. As illustrated in FIG. 18B, the ribs (e.g., rib 280) of the present disclosure further ensure that IV tube 120 may also be bent or twisted in multiple directions relative to the pump housing without fully collapsing, leaving a volume open to fluid flow.

Figure 19A:
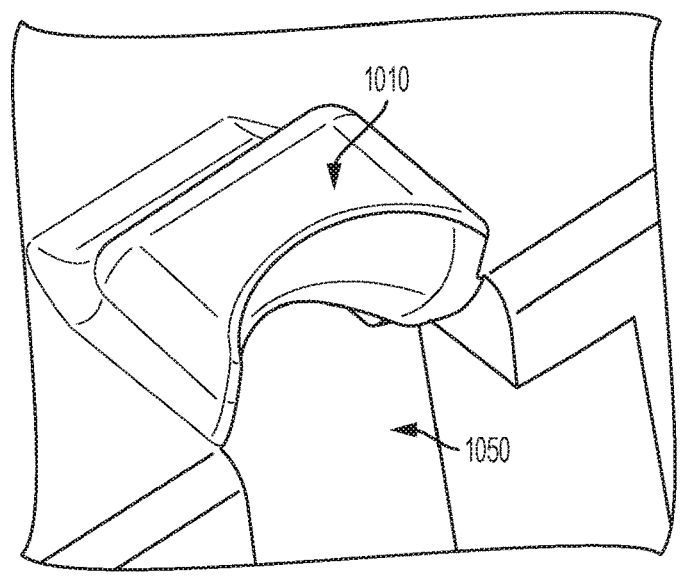
FIG. 19A is a top view of a tube port according to an example embodiment of the present disclosure.
Figure 19B:
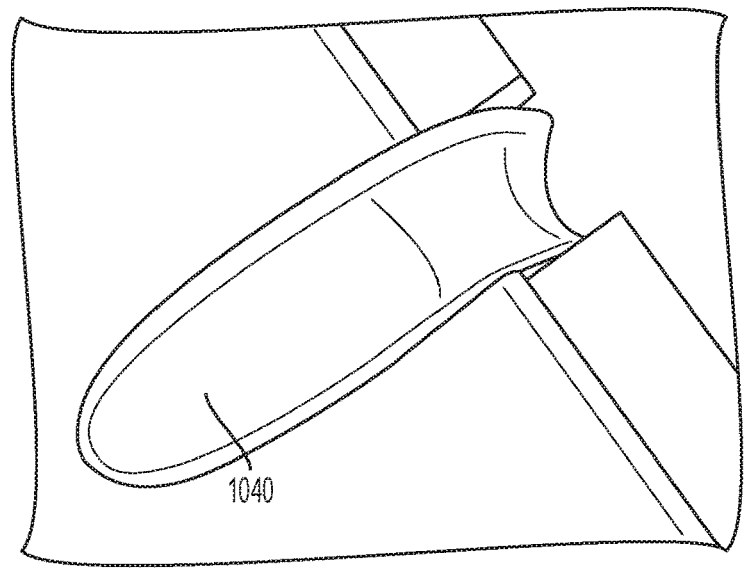
FIG. 19B is a bottom view of a tube port according to an example embodiment of the present disclosure.
Figure 19C:
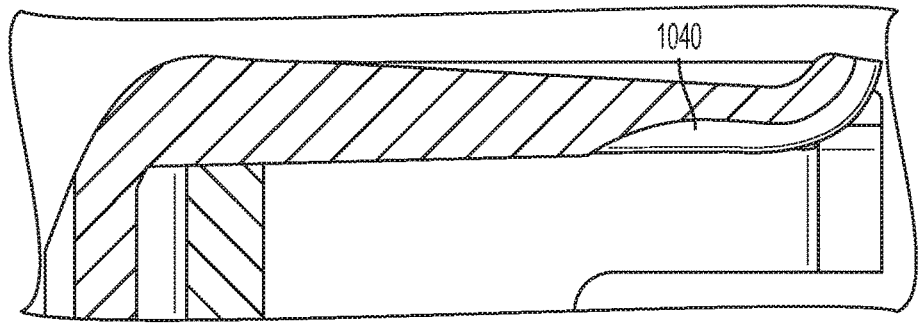
FIG. 19C is a sectional view of a tube port according to an example embodiment of the present disclosure.

Referring now to FIGS. 19A to 19C, in an alternative embodiment, housing 110 may include tube port 1050. Tube port 1050 may include a small rib, similar to rib 280. Alternatively, tube port 1050 does not provide a rib. Tube port 1050 may include tube channel 1040 that has a depth and width configured to provide support to the walls of tube 120 such that tube 120 does not fully occlude when exiting housing 110. Additionally, housing 110 may include a ridge 1010, which allows tube 120 to extend along tube channel 1040 for a greater distance, thereby enabling tube channel 1040 to support tube 120 and prevent tube collapse along a larger section of the tube.

The features disclosed herein also provide housing 110 with protection against water ingress. For example, as shown in Table 1 below, at least twenty tests have been performed, each showing that housing 110 with the anti-occlusion ribs of the present disclosure have passed the IPX2 test for water ingress. Housing 110 with the present ribs is thereby protected against water drops falling vertically onto the housing (e.g., from a drug supply bag), even when the enclosure (e.g., housing 110) is titled up to fifteen degrees. Vertically falling water drops therefore result in no harm to the infusion pump when its housing 110 is titled at any angle up to 15 degrees from either side of vertical.

TABLE 1

| Design Type | Tests | Passes | Failures |
| --- | --- | --- | --- |
| Anti-occlusion | 20 | 20 | 0 |

Additionally, flow rate accuracy ("FRA") tests have verified that there is no impact on flow rate accuracy (FRA) using the tube ports described herein. The test data below demonstrates that the FRA with an anti-occlusion rib performs better than designs without the anti-occlusion rib. As shown in Table 2, the anti-occlusion rib (e.g., rib 280) had the lowest percent error in flow rate when bending tube 120 at a one-hundred twenty degree angle. For example, the percent error in flow rate was about 0.20% for pumps employing the anti-occlusion rib compared to about 0.60%, 1.00%, and 2.00% for other housing configurations. Additionally, when bending tube 120 at a one-hundred twenty degree angle towards the back and 45 degrees to the side, the anti-occlusion rib (e.g., rib 280) had the lowest percent error in flow rate (e.g., about −6.00% vs −8.00%, −8.50%, and −11.00% respectively).

TABLE 2

| | | Percent Error | |
| --- | --- | --- | --- |
| Serial Number | Pump Descriptor | 120° back | 120° back, 45° to the side |
| 3000022 | Spectrum V9 F2a Pump with outer door removed (control unit) | 0.88% | −8.36% |
| 3000023 | Spectrum V9 F2a with anti-occlusion rib | 0.115% | −6.15% |
| 2002267 | Spectrum V8 (control unit) | 0.561% | −10.91% |
| 3000022 | Pump with outer door removed (control unit) | 1.00% | −8.50% |
| 3000024 | Pump with rounded "funnel" | 2.00% | −8.00% |
| 3000023 | Pump with anti-occlusion rib | 0.20% | −6.00% |
| 2002267 | Prior Pump (control unit) | 0.60% | −11.00% |

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. An infusion pump comprising:
   a housing including a tube port configured to receive an intravenous ("IV") tube, wherein the tube port includes
      a tube channel having an inlet end located within the housing, an outlet end located at an edge of the housing, and a length between the inlet and outlet ends, and
      a rib positioned along the tube channel adjacent to the outlet end, wherein the rib is formed to extend outwardly from a surface of the tube channel to split the tube channel into at least two parallel channels along at least a portion of the length of the tube channel.

2. The infusion pump of claim 1, wherein the at least two parallel channels are configured to accept respective parallel tube regions to prevent fluid occlusion within the IV tube when the IV tube is pressed against the rib.

3. The infusion pump of claim 1, wherein the tube channel is positioned along an interior wall of the housing.

4. The infusion pump of claim 1, wherein the tube channel is configured to cradle a portion of the IV tube.

5. The infusion pump of claim 1, which is configured such that the IV tube extends along the tube channel when the IV tube is pressed through the tube port.

6. A housing for an infusion pump comprising:
   a tube port configured to receive an intravenous ("IV") tube, wherein the tube port includes
      a tube channel having an inlet end, an outlet end, and a length between the inlet and outlet ends, and
      a rib positioned along at least a portion of the length of the tube channel adjacent to the outlet end, wherein the rib is formed to extend outwardly from a surface of the tube channel towards the IV tube, thereby indenting the IV tube to form at least two parallel tube regions in the IV tube and tending to prevent full occlusion of the IV tube.

7. The housing of claim 6, wherein the rib is configured to split the tube channel into a first channel and a second channel.

8. The housing of claim 7, wherein the first and second channels are configured to respectively accept the at least two parallel tube regions.

9. The housing of claim 6, wherein the tube channel is positioned along an interior wall of the housing.

10. The housing of claim 6, wherein the rib includes a first end and a second end, the first end having a first diameter and the second end having a second, different diameter.

11. The housing of claim 10, wherein the second diameter is larger than the first diameter.

12. The housing of claim 6, wherein the rib includes a gradually increasing extension from the surface of the tube channel from a first end to a second end, the first end closer to an outside opening of the tube port than the second end.

13. The housing of claim 6, wherein the formation of the at least two parallel tube regions prevents fluid occlusion within the IV tube when the IV tube is pressed against the rib.

14. The housing of claim 6, wherein the rib is positioned on an interior side of the housing.

15. The housing of claim 6, wherein the rib is positioned on an exterior side of the housing.

16. An infusion pump comprising:
a housing including a tube port configured to receive an intravenous ("IV") tube; and
a plurality of ribs positioned around a perimeter of the tube port on an exterior side of the housing, the plurality of ribs formed along a fluid flow path of the IV tube and configured to prevent an occlusion in the IV tube when the IV tube is bent on the exterior side of the housing.

17. The infusion pump of claim 16, wherein the plurality of ribs are circumferentially positioned around the perimeter and are each pointed towards a center of the tube port.

18. The infusion pump of claim 16, wherein each of the plurality of ribs has at least approximately the same size and shape.

19. The infusion pump of claim 16, wherein the plurality of ribs includes a first rib and a second rib, the first rib having a different shape, size and/or orientation than the second rib.

20. The infusion pump of claim 16, wherein each of the plurality of ribs extends radially towards a center of the tube port.

\* \* \* \* \*